US010201405B2

(12) United States Patent
Bellanca et al.

(10) Patent No.: US 10,201,405 B2
(45) Date of Patent: Feb. 12, 2019

(54) SYSTEM AND METHOD OF DENTAL IMPLANT AND INTERFACE TO ABUTMENT FOR RESTORATION

(75) Inventors: John J. Bellanca, West Palm Beach, FL (US); Dan P. Rogers, North Palm Beach, FL (US); Stephen M. Herrington, Naples, FL (US); Ross W. Towse, Palm City, FL (US); Ralph E. Goodman, West Palm Beach, FL (US); Zachary B. Suttin, Palm Beach Gardens, FL (US); Isabel Scalise, West Palm Beach, FL (US); Michael Bobby, Boynton Beach, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 63 days.

(21) Appl. No.: 13/533,406

(22) Filed: Jun. 26, 2012

(65) Prior Publication Data
US 2013/0004915 A1 Jan. 3, 2013

Related U.S. Application Data

(60) Provisional application No. 61/502,091, filed on Jun. 28, 2011.

(51) Int. Cl.
A61C 8/00 (2006.01)
(52) U.S. Cl.
CPC ............ *A61C 8/0089* (2013.01); *A61C 8/006* (2013.01); *A61C 8/0018* (2013.01);
(Continued)
(58) Field of Classification Search
CPC ....... A61C 8/005; A61C 8/006; A61C 8/0018; A61C 8/0054; A61C 8/0069
(Continued)

(56) References Cited

U.S. PATENT DOCUMENTS 5,447,434 A * 9/1995 Shaw ........................... 433/173
5,527,182 A * 6/1996 Willoughby ................. 433/172
(Continued)

FOREIGN PATENT DOCUMENTS

CA 2230615 8/1997 ............... A61C 8/00
DE 3300764 7/1984 ............... A61C 8/00
(Continued)

OTHER PUBLICATIONS

English language machine translation of DE 44 05 797 C1. May 18, 1995.*
(Continued)

Primary Examiner — Yogesh Patel
Assistant Examiner — Matthew Saunders
(74) Attorney, Agent, or Firm — Schwegman Lundberg & Woessner, P.A.

(57) ABSTRACT

A dental assembly for vertical attachment of an implant to a dental abutment for restorative dental procedures is disclosed. The implant includes a cylindrical body having an interior bore formed between a distal end and a proximal end. An abutment interface is formed on the proximal end of the cylindrical body. The interface includes a radial annular interior surface and a flat annular stop surface circumferentially bordering the interior bore. The assembly also includes an abutment including a stem and a post coupled to the stem. An interior bore is formed through the stem and the post. The abutment includes an interface section between the post and the stem. The interface section may include an annular radially curved exterior surface proximate to the post. The radially curved exterior surface and the circular flat surface interfaces with the abutment interface of the dental implant.

8 Claims, 11 Drawing Sheets

(52) U.S. Cl.
CPC .......... *A61C 8/0057* (2013.01); *A61C 8/0059* (2013.01); *A61C 8/0066* (2013.01); *A61C 8/0068* (2013.01); *A61C 8/0022* (2013.01)

(58) Field of Classification Search
USPC ................................................ 433/172–176
See application file for complete search history.

(56) References Cited

U.S. PATENT DOCUMENTS

| | | | | |
|---|---|---|---|---|
| 5,695,335 A * | 12/1997 | Haas et al. | .................... | 433/173 |
| 5,823,776 A * | 10/1998 | Duerr et al. | .................... | 433/173 |
| 5,888,218 A * | 3/1999 | Folsom | ...................... | 623/16.11 |
| D414,556 S | 9/1999 | Broberg et al. | ............. | D24/156 |
| 5,952,399 A | 9/1999 | Rentsch | ........................ | 523/116 |
| 5,954,504 A | 9/1999 | Misch et al. | .................. | 433/174 |
| 5,954,505 A | 9/1999 | Ford | ............................. | 433/177 |
| 5,961,328 A | 10/1999 | Somborac et al. | ........... | 433/173 |
| 5,961,329 A | 10/1999 | Stucki-McCormick | ...... | 433/173 |
| 5,964,591 A | 10/1999 | Beaty et al. | .................. | 433/173 |
| 5,975,902 A | 11/1999 | Emmanuel | .................... | 433/173 |
| 5,979,643 A | 11/1999 | Blonder et al. | ............. | 206/63.5 |
| 5,984,680 A | 11/1999 | Rogers | .......................... | 433/173 |
| 5,989,028 A | 11/1999 | Niznick | ......................... | 433/173 |
| 5,989,029 A | 11/1999 | Osorio et al. | ................. | 433/173 |
| 5,993,211 A | 11/1999 | Broberg | ........................ | 433/172 |
| 5,993,214 A | 11/1999 | Persson | ........................ | 433/223 |
| 6,007,337 A | 12/1999 | Bauer | ............................ | 433/173 |
| 6,012,923 A | 1/2000 | Bassett et al. | ................ | 433/172 |
| 6,030,219 A | 2/2000 | Zuest et al. | ................... | 433/181 |
| 6,033,218 A | 3/2000 | Bergström et al. | ............ | 433/72 |
| 6,036,491 A | 3/2000 | Hansson | ....................... | 433/174 |
| 6,039,568 A | 3/2000 | Hinds | ........................... | 433/175 |
| 6,045,361 A | 4/2000 | Misch et al. | .................. | 433/214 |
| 6,048,204 A | 4/2000 | Klardie et al. | ................ | 433/174 |
| 6,053,733 A | 4/2000 | Aspichueta et al. | .......... | 433/173 |
| 6,053,920 A | 4/2000 | Carlsson et al. | ............... | 606/72 |
| 6,066,274 A | 5/2000 | Antonson et al. | ............ | 264/16 |
| 6,068,478 A | 5/2000 | Grande et al. | ................. | 433/172 |
| 6,068,479 A | 5/2000 | Kwan | ............................ | 433/173 |
| 6,068,480 A | 5/2000 | Misch et al. | .................. | 433/173 |
| 6,076,660 A | 6/2000 | Day | .............................. | 206/63.5 |
| 6,168,436 B1 * | 1/2001 | O'Brien | ......................... | 433/173 |
| 6,257,890 B1 * | 7/2001 | Khoury | .................. | A61C 8/008 |
| | | | | 433/173 |
| 6,261,097 B1 | 7/2001 | Schmutz et al. | .............. | 433/173 |
| 6,261,098 B1 | 7/2001 | Persson | ........................ | 433/213 |
| D446,859 S | 8/2001 | Hurson | ........................ | D24/156 |
| 6,273,720 B1 | 8/2001 | Spalten | ......................... | 433/173 |
| 6,273,722 B1 | 8/2001 | Phillips | ......................... | 433/174 |
| 6,276,938 B1 | 8/2001 | Jörneus et al. | ................ | 433/172 |
| 6,280,195 B1 | 8/2001 | Broberg et al. | ............. | 433/201.1 |
| 6,283,752 B1 | 9/2001 | Kumar | .......................... | 433/172 |
| 6,283,755 B1 | 9/2001 | Bergström et al. | ........... | 433/193 |
| 6,287,119 B1 | 9/2001 | van Nifterick et al. | ...... | 433/213 |
| 6,290,499 B1 | 9/2001 | Lazzara et al. | ............... | 433/173 |
| 6,290,500 B1 | 9/2001 | Morgan et al. | ............... | 433/173 |
| 6,305,938 B1 | 10/2001 | Brånemark | ................... | 433/173 |
| 6,305,939 B1 | 10/2001 | Dawood | ....................... | 433/174 |
| 6,312,260 B1 | 11/2001 | Kumar et al. | ................. | 433/174 |
| 6,315,562 B1 | 11/2001 | Kumar | .......................... | 433/173 |
| 6,315,563 B1 * | 11/2001 | Sager | ............................ | 433/173 |
| 6,332,777 B1 | 12/2001 | Sutter | ........................... | 433/173 |
| 6,343,930 B1 | 2/2002 | Beaty et al. | .................. | 433/173 |
| 6,350,126 B1 | 2/2002 | Levisman | ..................... | 433/173 |
| 6,358,050 B1 | 3/2002 | Bergström et al. | ........... | 433/173 |
| 6,358,051 B2 | 3/2002 | Lang et al. | .................... | 433/173 |
| 6,358,052 B1 | 3/2002 | Lustig et al. | .................. | 433/174 |
| 6,375,464 B1 * | 4/2002 | Hollander et al. | ............ | 433/173 |
| 6,382,976 B1 | 5/2002 | Wagner | ........................ | 433/174 |
| 6,394,803 B1 | 5/2002 | Salz et al. | ........................ | 433/49 |
| 6,394,806 B1 | 5/2002 | Kumar | .......................... | 433/173 |
| 6,394,809 B2 | 5/2002 | Rogers et al. | ................. | 433/174 |
| 6,402,515 B1 | 6/2002 | Palti et al. | ..................... | 433/174 |
| 6,619,958 B2 | 9/2003 | Beaty et al. | .................. | 433/173 |
| 6,666,685 B2 | 12/2003 | Filho | ............................. | 433/173 |
| 2004/0101808 A1 * | 5/2004 | Porter et al. | .................. | 433/173 |
| 2008/0261176 A1 * | 10/2008 | Hurson | ......................... | 433/174 |
| 2010/0119995 A1 * | 5/2010 | Grant et al. | ................... | 433/174 |
| 2013/0004916 A1 | 1/2013 | Bellanca et al. | ............... | 433/173 |

FOREIGN PATENT DOCUMENTS

| | | | |
|---|---|---|---|
| DE | 4028855 | 3/1992 | ............. A61C 8/00 |
| DE | 4405797 C1 * | 5/1995 | |
| EP | 0231730 | 8/1987 | ............. A61C 8/00 |
| EP | 0475299 | 3/1992 | ............. A61C 8/00 |
| EP | 0497082 | 8/1992 | ............. A61C 8/00 |
| EP | 0657146 | 6/1995 | ............. A61C 8/00 |
| EP | 0727193 | 8/1996 | ............. A61C 8/00 |
| EP | 0735843 | 10/1996 | ............. A61C 8/00 |
| FR | 2635455 | 2/1990 | ............. A61C 8/00 |
| WO | 93/20773 | 10/1993 | ............. A61C 8/00 |
| WO | 94/14388 | 7/1994 | ............. A61C 8/00 |
| WO | 96/29019 | 9/1996 | ............. A61C 8/00 |
| WO | 97/06930 | 2/1997 | ............. A61C 8/00 |
| WO | 97/10769 | 3/1997 | ............. A61C 8/00 |
| WO | 97/24977 | 7/1997 | ............. A61C 8/00 |
| WO | 97/28755 | 8/1997 | ............. A61C 8/00 |
| WO | 98/03130 | 1/1998 | ............. A61C 8/00 |
| WO | 98/52490 | 11/1998 | ............. A61C 8/00 |
| WO | 98/55039 | 12/1998 | ............. A61C 8/00 |
| WO | 99/08620 | 2/1999 | ............. A61C 8/00 |
| WO | 00/02497 | 1/2000 | ............. A61C 8/00 |
| WO | WO 2010066871 A1 * | 6/2010 | |

OTHER PUBLICATIONS

English translation of WO 2010066871 A1, Jun. 17, 2010.*
OSPOL. Abutment Remover. [online], [retrieved on Sep. 26, 2012]. Retrieved from the Internet URL: <http://www.ospol.com/?id=1304>.
International Search Report and Written Opinion dated Sep. 24, 2012 issued in International Patent Application No. PCT/US2012/044308 (13 pages).

* cited by examiner

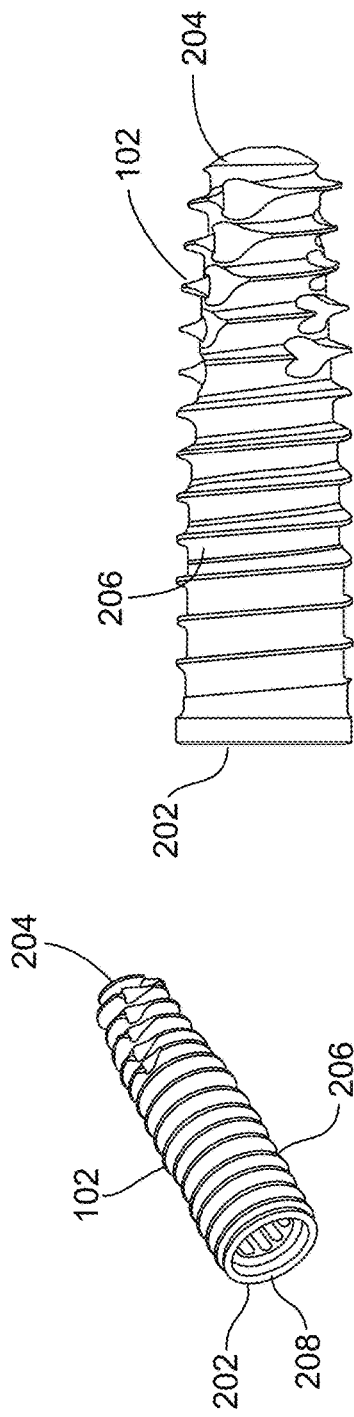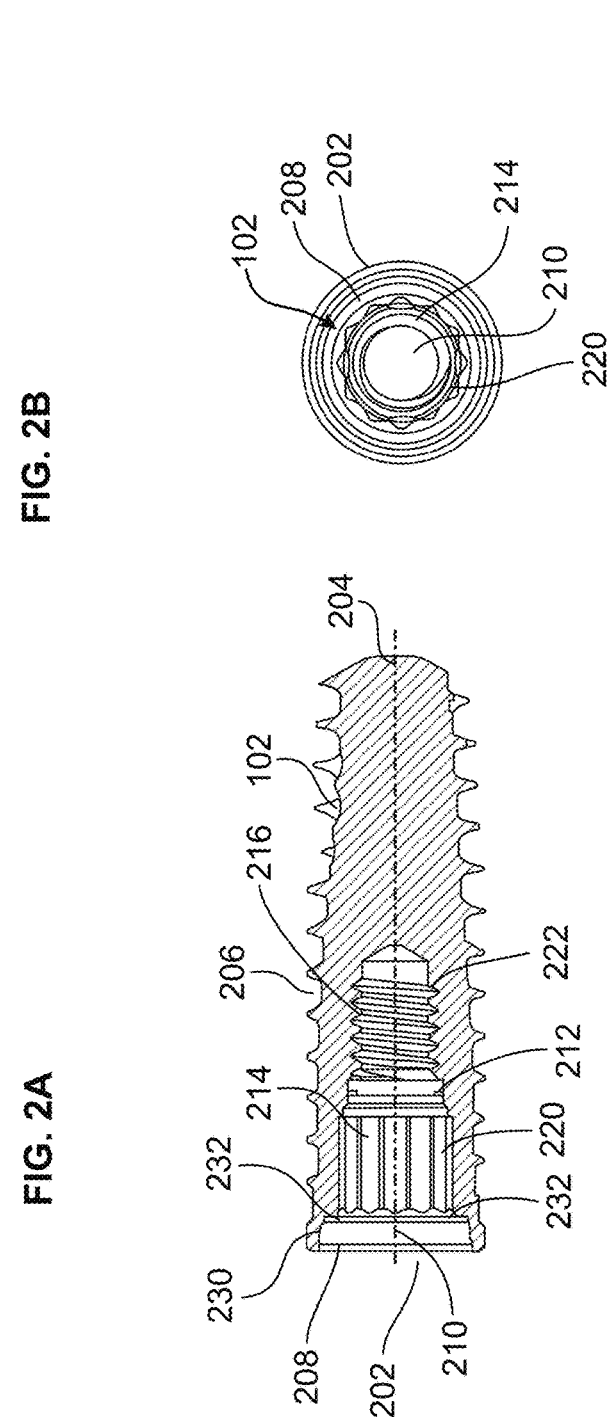

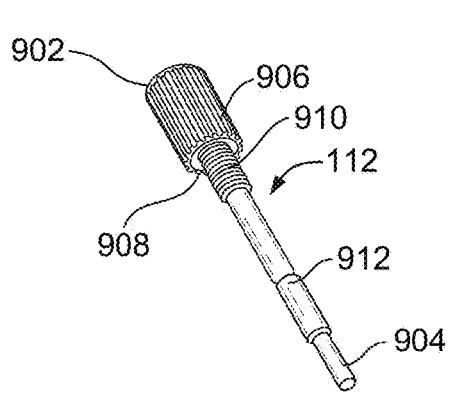
FIG. 9A
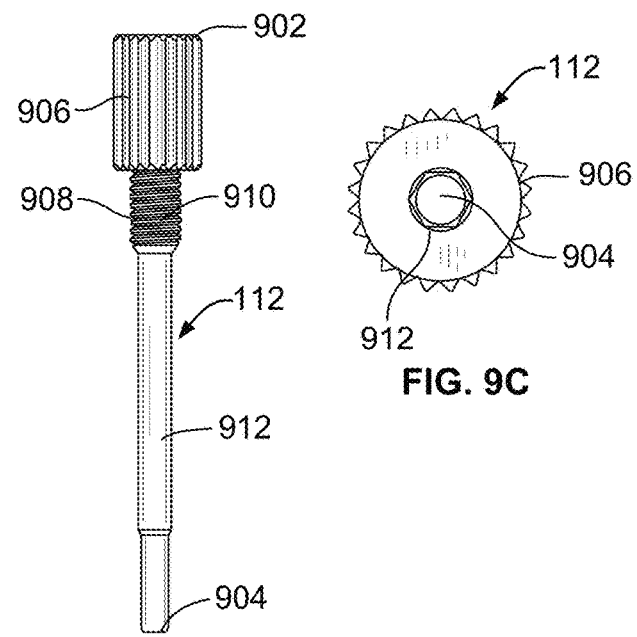
FIG. 9C
FIG. 9B
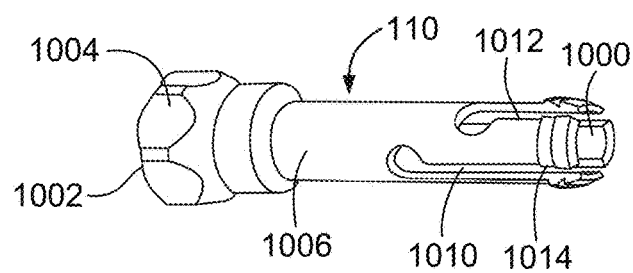
FIG. 10A
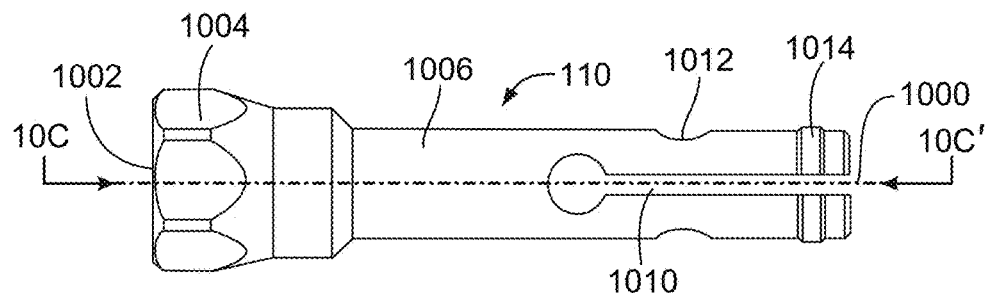
FIG. 10B

SYSTEM AND METHOD OF DENTAL IMPLANT AND INTERFACE TO ABUTMENT FOR RESTORATION

PRIORITY CLAIM AND CROSS REFERENCE TO RELATED APPLICATIONS

This application claims priority to U.S. Provisional Application No. 61/502,091, filed on Jun. 28, 2011 which is incorporated herein its entirety.

TECHNICAL FIELD

This disclosure relates to restorative dental implants and abutments and related tools for the assembly and disassembly of the same.

BACKGROUND

Single tooth restorations present the unique requirement that they must be supported non-rotationally on an underlying abutment. When a prepared natural tooth is the underlying abutment, this requirement is met in the normal course of preparing the abutment with a non-circular cross-section. Likewise, when the underlying abutment is a post fitted onto an implant, this requirement is met by preparing the post with a noncircular cross-section. This latter scenario can be more complicated due to the added connection between the implant and the abutment.

Typically, a dental implant is implanted into the bone of a patient's jaw and comprises a socket, e.g., a bore, which is accessible through the overlying or surrounding gum tissue for receiving and supporting one or more attachments or components which, in turn, are useful to fabricate and support the prosthodontic restoration. Dental implant procedures may use a variety of implanting modalities, for example, blade, threaded implant, or smooth push-in implant.

While numerous design iterations have been marketed, overall there have been three generations of the implant-abutment interface within these assemblies: an external hex implant, an internal connection implant, and a vertical connection assembly. The external hexagonal implant design has a hexagonal shape (or another anti-rotation feature) protruding out of the implant and the corresponding abutment has a female hexagonal receptacle. There is a surface below the hexagonal protrusion on which the abutment is seated. The hexagonal protrusion acts to constrain the abutment from rotating around the longitudinal axis as well as preventing movement on the plane coincident with the implant seating surface. Unfortunately, such an interface has virtually no stability until the screw is introduced and fully seated between the abutment and the implant. The screw is essentially the sole component resisting bending forces.

In contrast, the internal connection implant design has a hexagonal female member (or other anti-rotation feature) extruded into the implant, and the corresponding abutment has a male hexagonal protrusion. The abutment is seated on the same surface as the external hexagonal design, the only difference being that the anti-rotation feature on the implant is located below this surface. The benefit of this system is that it has intrinsic stability without the screw, and then experiences increased stability once the screw is introduced and fully seated. The system responds in a more unified manner to bending forces. While this system has advantages over the external hex implant, the disadvantage (which applies to the external hex as well) is that it is prone to leak at the implant-abutment interface (seating surface) due to "lifting" of the abutment under load that may create an intermittent gap resulting in bacteria penetration and subsequent crestal bone loss.

Another alternative interface is an internal/vertical connection implant assembly where the abutment sits "vertically" within the implant assembly and is supported by the internal sidewalls. In addition to this vertically interfacing aspect, many abutments contain a male anti-rotation feature at the bottom and the corresponding implants have a female receptacle (similar to the internal connection implant design). The main benefits of this design are that the two components effectively wedge together, creating a seal impenetrable to bacteria and the abutment receives added lateral support from the implant due to interaction of the abutment sidewalls with the interior surfaces of the implant. However, such designs suffer from vertical location variability. The accuracy of the fit of the final implant restoration (i.e., crown) is largely dependent on the ability to reliably transfer the location of the implant throughout the multiple steps involved in fabricating the restoration. The currently marketed vertical connection implant systems are susceptible to significant vertical location variability, and subsequent customer dissatisfaction. Location variability is undetectable until the very last step in the restorative process when the patient receives their restoration where it becomes apparent the restoration is too high or too low relative to the original tooth. For example, due to the required manufacturing tolerances, each time an abutment (or other male part) is mated with an implant (or other female part) the initial vertical position is destined to change. Further, once the parts are mated and torque is applied to the screw attaching the abutment to the implant, there is relative motion (or vertical displacement) between the male and female components. The magnitude of this motion is dependent on multiple variables, including but not limited to the screw torque, the surface finishes, and the component specifications.

Known vertical implant systems therefore still allow the lateral movement of the abutment in relation to the implant thus causing the possibility of misalignment. It would be desirable to have an abutment implant interface that eliminates vertical location variability. As the vertical connection implant assembly becomes accepted, it is necessary to develop a system that maintains the benefits of this type of design, yet eliminates the known vertical location variability problem. It would also be desirable for a system to create seals between the abutment and implant. The increase in seals in a contemplated system may result in adhesion between the implant and the abutment. Therefore it would be desirable for a removal system to assist in the removal of an abutment that adheres to an implant due to an improved interface.

BRIEF SUMMARY

An aspect of the present disclosure is an abutment for use in conjunction with a dental implant. The abutment includes a stem and a post opposite of the stem. An interior bore is formed through the stem and the post. An interface section is formed between the post and the stem. The interface section has an annular radially curved exterior surface proximate to the post. The annular radially curved exterior surface interfaces with the dental implant.

Another disclosed aspect is a dental implant for use in conjunction with an abutment. The implant includes a cylindrical body having an interior bore formed between a distal end and a proximal end. An abutment interface is located on the proximal end of the cylindrical body. The interface includes a radial annular interior surface bordering the interior bore. An anti-rotational cavity is formed in the interior bore proximal to the interface.

Another disclosed aspect is a dental restoration system including an abutment and an implant. The implant attaches to a jaw bone of a patient. The implant includes a cylindrical body having an interior bore formed between a distal end and a proximal end. An abutment interface is located on the proximal end of the cylindrical body. The interface includes a radial annular interior surface circumferentially bordering the interior bore. An anti-rotational cavity is formed in the interior bore proximal to the interface. The abutment includes a stem and a post opposite the stem. An interior bore is formed through the stem and the post. An interface section is located between the post and the stem. The interface section has an annular radially curved exterior surface proximate to the post. The radially curved exterior surface interfaces with the abutment interface of the dental implant.

Another aspect of the disclosure is an abutment for use in conjunction with a dental implant. The abutment includes a stem and a post opposite the stem. An interior bore is formed through the stem and the post. An interface section is located between the post and the stem. The interface section has an exterior surface proximate to the post. The exterior surface terminates into a circular flat surface. The post extends from the circular flat surface. An annular groove is cut into the circular flat surface to allow compliant fit of the interface section with a mating interface surface of the implant.

The foregoing and additional aspects and implementations of the present disclosure will be apparent to those of ordinary skill in the art in view of the detailed description of various embodiments and/or aspects, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

FIG. 2A is a perspective view of the dental implant with a vertical abutment interface shown in FIG. 1;

FIG. 2B is a side view of the implant shown in FIG. 2A;

FIG. 2C is a cross-section side view of the implant shown in FIG. 2A;

FIG. 2D is a view of the distal end of the implant shown in FIG. 2A;

FIG. 9A is a perspective view of the abutment removal tool screw shown in FIG. 1;

FIG. 9B is a side view of the abutment removal tool screw shown in FIG. 9A;

FIG. 9C is a front view of the abutment removal tool screw shown in FIG. 9A;

FIG. 10A is a perspective view of the abutment removal tool insert shown in FIG. 1;

FIG. 10B is a side view of the abutment removal tool insert shown in FIG. 10A;

Figure 1:
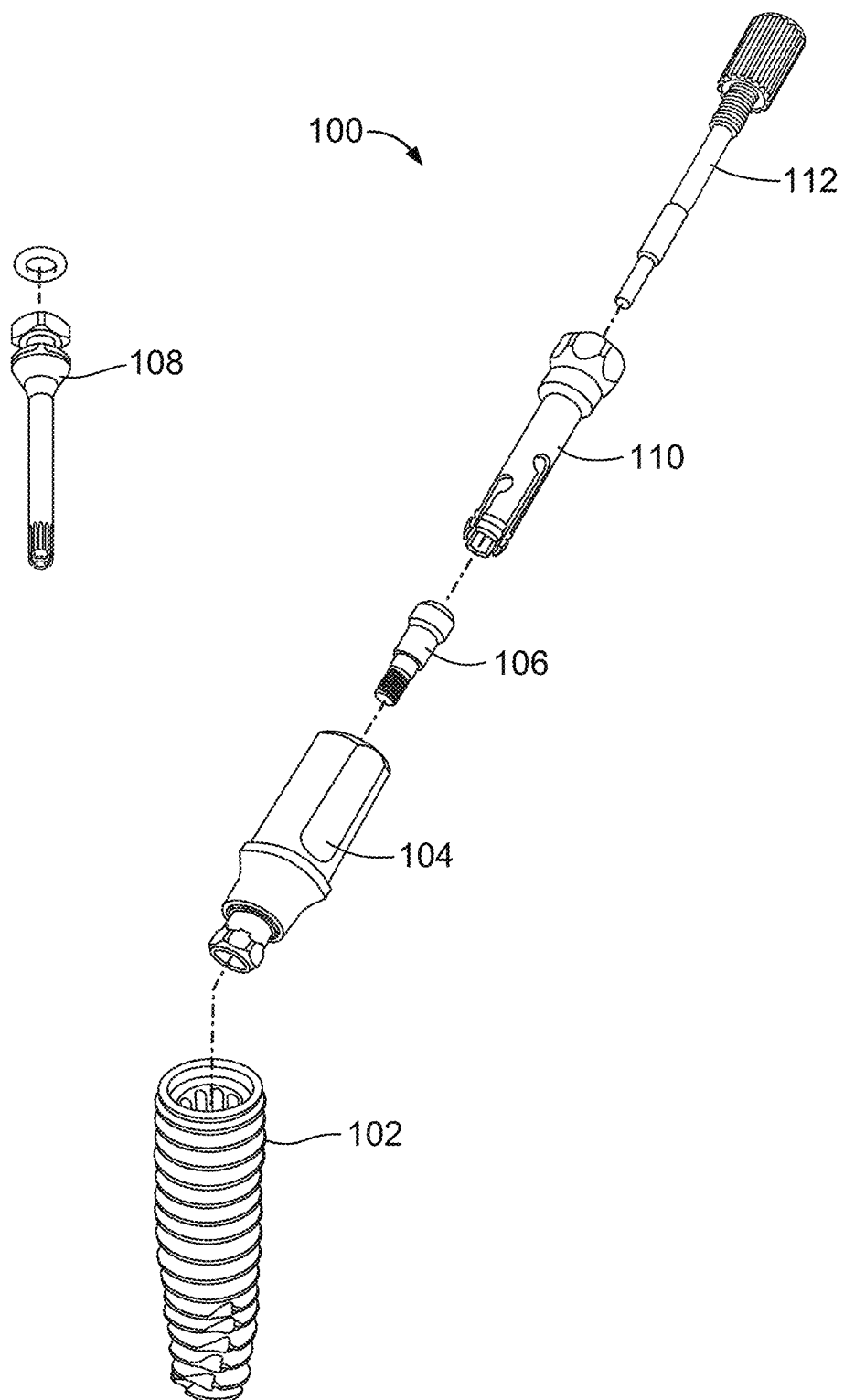
FIG. 1 is an exploded perspective view of an implant and abutment dental restoration system including an implant, an abutment, an insert screw, an implant driver, a removal tool, and a removal tool screw.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

FIG. 1 is an exploded perspective view of the implant and abutment installation system 100 including an implant 102, an abutment 104, an abutment screw 106, and an implant driver tool 108. FIG. 1 also shows a removal system for the abutment 104 including an abutment removal insert tool 110, and an abutment removal tool screw 112. The components shown in FIG. 1 are used in dental restorative processes. As is known, the implant 102 is implanted into the bone of a patient's jaw. The implant driver tool 108 is used to fix the implant 102 into the bone. The abutment 104 may be a standard part or customized to replace the patient's tooth and is attached to the implant 102. The abutment 104 is fixed to the implant 102 via the abutment screw 106, which may be installed via a screw driver tool. In cases where the abutment 104 must be removed from the implant 102 and cannot be readily removed by hand (after the abutment screw 106 is removed), the abutment removal insert tool 110 is used in conjunction with the removal tool screw 112 to remove the abutment 104 without displacing and or rotating the implant 102.

The implant 102 is further detailed in FIGS. 2A-2D where FIG. 2A is a perspective view of the implant 102, FIG. 2B is a side view of the implant 102, FIG. 2C is a cross-section side view of the implant 102, and FIG. 2D is a view of the distal end of the implant 102. The implant 102 comprises a proximal end 202, a distal end 204 opposite the proximal end 202 and at least one thread 206 disposed therebetween for screwing the implant 102 into the bone of a patient. The proximal end 202 includes an interface 208 adapted to guide the abutment 104 in FIG. 1 when seating the abutment 104 in the implant 102. The implant 102 also includes an interior bore 210 that extends distally from the proximal end 202 toward the distal end 204. The interior bore 210 includes a first anti-rotation cavity 214 and a second anti-rotation cavity 216 distal of the first anti-rotation cavity 214. The interface 208 is concentrically located around the interior bore 210 and is proximal to the first anti-rotation cavity 214. A counter bore 212 is formed between the two cavities 214 and 216.

As shown in detail in FIG. 2C, the two cavities 214 and 216 are separate, distinct and slightly spaced apart, and are connected with a series of concentric steps including the counter bore 212. Other arrangements, however, are equally suitable, such as, for example, where the cavities are adjacent with a tapered transition, or spaced apart and connected by one or more cavities. As will be explained below, the counter bore 212 is fabricated at a narrower diameter than the first cavity 214 to assist in fixing an implant driver tool such as the implant driver tool 108 in FIG. 1 to the implant 102.

Focusing on FIGS. 2C and 2D, the first anti-rotation cavity 214 of implant 102 includes a multi-sided socketed interior surface 220. The socketed interior surface 220 has a plurality of obtuse interior angles in a double hexagonal shape, but other socket shapes may be used. The second anti-rotation cavity 216 includes a threaded interior surface 222 that accepts the abutment screw 106 in FIG. 1.

For some applications, at least one of the anti-rotation cavities 214 and 216 is adapted to mate with a conventional driving tool, for example, a tool with a working end comprising a square, a pentagon, a hexagon, an octagon, etc. Some tools are described in detail such as the implant driver tool 108 shown in detail in FIGS. 8A-8C and the implant driver tool 1200 shown in detail in FIGS. 12A-12B. The cavities 214 or 216 may also be used to hold the abutment 104. However, the other cavity may be adapted to mate with an abutment stem having a predetermined shape other than the cavity that holds the driving tool.

The interface 208 is cylindrically shaped having an interior surface ending in a radially curved annular inner surface 230 proximate the first anti-rotation cavity 214. The annular inner surface 230 transitions to a flat circular vertical stop surface 232 that borders the first cavity 214. As will be explained below, the radially curved inner surface 230 and the vertical stop surface 232 function to guide the abutment 104 and prevent vertical location variability of the abutment 104 relative to the implant 102. The contact of the inner surface 230 and the vertical stop surface 232 of the interface 208 also form seals to prevent gaps in the interface between the implant 102 and the abutment 104.

Figure 3A:
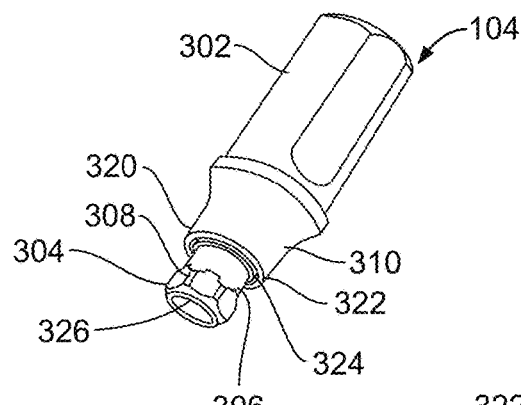
FIG. 3A is a perspective view of the abutment with a vertical implant interface shown in FIG. 1.
Figure 3B:
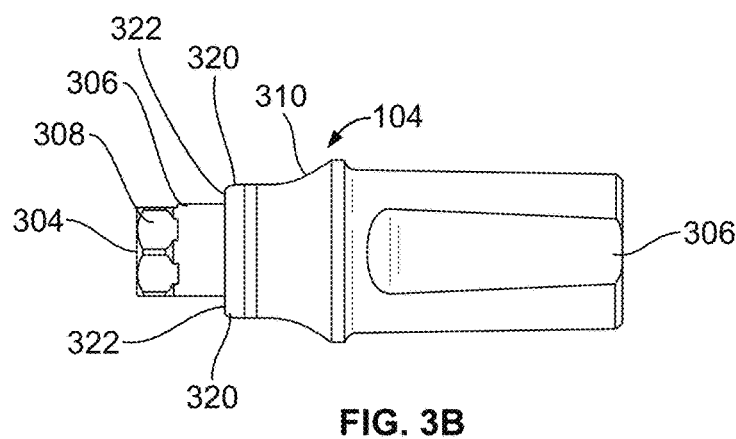
FIG. 3B is a side view of the abutment shown in FIG. 3A.
Figure 3C:
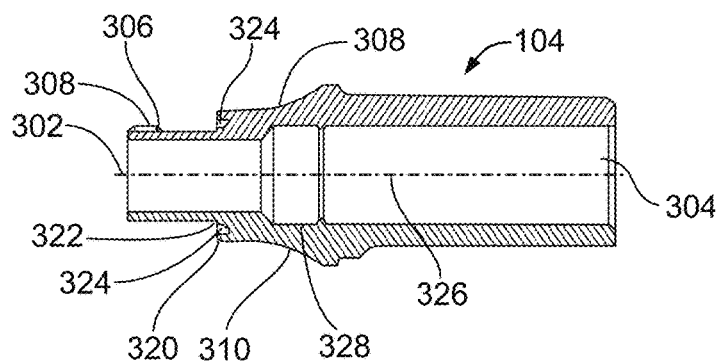
FIG. 3C is a cross-section side view of the abutment shown in FIG. 3A.
Figure 3D:
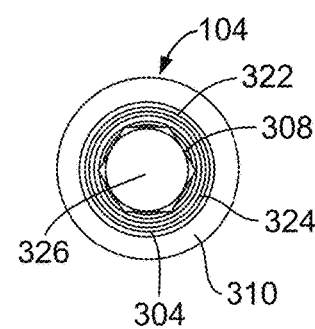
FIG. 3D is a front view of the abutment shown in FIG. 3A.

FIG. 3A-3D are views of the abutment 104 shown in FIG. 1 where FIG. 3A is a perspective view of the abutment 104, FIG. 3B is a side view of the abutment 104, FIG. 3C is a cross-section side view of the abutment 104, and FIG. 3D is a front view of the abutment 104. The abutment 104 comprises a post 302 and a stem 304 extending in a relative downward direction from the post 302. The stem 304 includes a locking portion 306 adapted to be positioned in the first anti-rotation cavity 214 when the abutment 104 is positioned in the implant 102. Accordingly, the locking portion 306 has a multi-sided exterior surface 308 that is adapted to rotationally-lockingly engage the interior multi-sided socketed surface 220 of the first anti-rotation cavity 214 in FIG. 2C, wherein the abutment 104 is prevented from rotating relative to the implant 102.

The abutment 104 includes a transitional section 310 between the post 302 and the stem 304. The transitional section 310 is roughly conical in shape with a larger end connected to the post 302 and an opposite smaller end connected to the stem 304. The smaller end of the transitional section 310 mates with the interface 208 of the implant 102 in FIGS. 2A-2D. The transitional section 310 includes an outer surface that has a curved shape from the larger end with the larger diameter closest to the post 302 to the opposite end with a smaller diameter connected to the stem 304. A radially shaped annular outer surface 320 terminates at the smaller end of the transitional section 310. The outer surface 320 forms a circular vertical stop surface 322 forming the bottom of the transitional section 310 from which the stem 304 protrudes. The circular vertical stop surface 322 includes a circular groove 324 that is cut into the transitional section 310. The circular groove 324 in this example is cut to a depth of approximately 0.012 inches. The circular groove 324 may be cut to a depth of 0.010 to 0.020 inches or deeper or shallower if desired.

In the abutment 104, a through-bore 326 extends through the post 302, the stem 304, and the transitional section 310 to allow the abutment screw 106 shown in FIG. 1 to be inserted therein. The abutment screw 106 is inserted into the through-bore 326 in the abutment 104 to threadably engage the threads of the interior surface 222 of the implant 102 as shown in FIG. 2C. The through-bore 326 also includes a groove 328 that is formed to roughly mate with the abutment removal insert tool 110 as will be explained below.

In FIG. 1, the abutment screw 106 includes a screw head adapted to mate with a driving tool (not shown) with a screw head such as an Allen wrench, a square driver, a flat head screwdriver, a Phillips screwdriver, etc. After the abutment 104 is placed in the implant 102, the abutment screw 106 is inserted in the through-bore 326 of the abutment 104 and the cavity 216 of the implant 102. The driving tool is used to tighten the abutment screw 106 by engaging the threaded interior surface 222 of the cavity 216. After the abutment screw 106 threadably engages the implant 102, the abutment screw 106 acts to retain the abutment 104 in the implant 102.

Figure 4A:
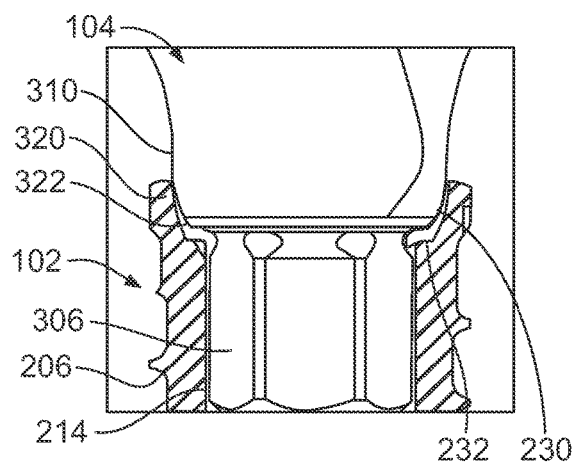
FIG. 4A-B are perspective side cutaway views of the initial contact and final contact between abutment and implant in FIG. 1 when seating the abutment in the implant.
Figure 4B:
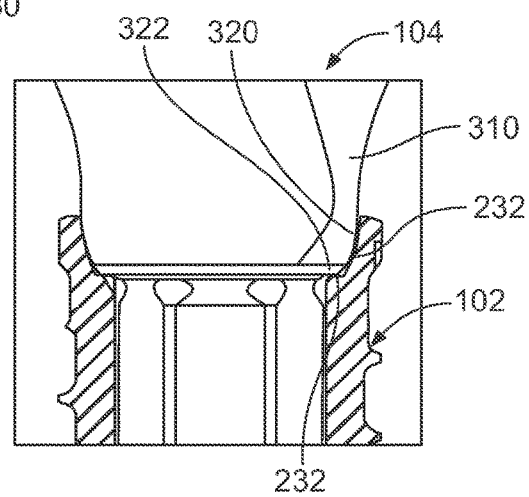
Figures 5A, 5B, 5C:
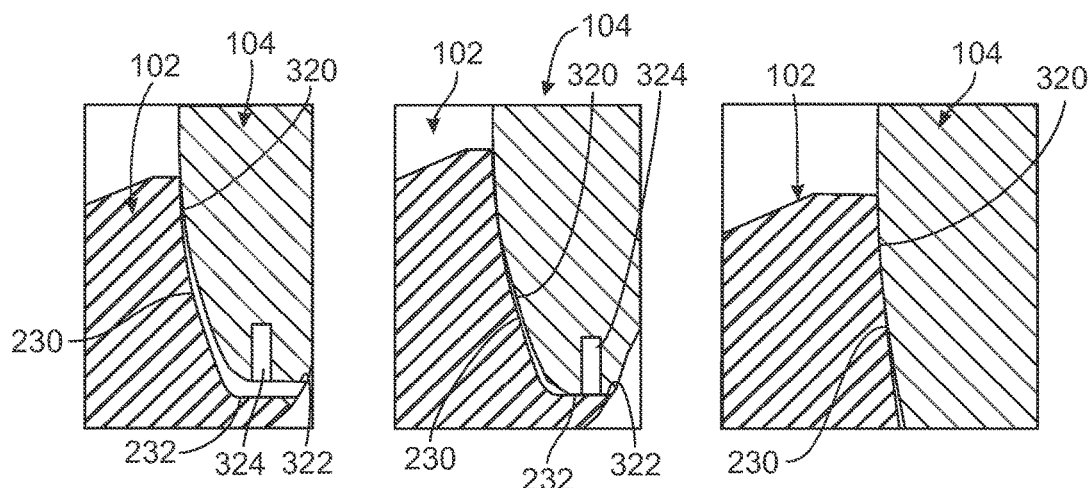
FIG. 5A-C are side cutaway views of the contacts between the abutment and implant in FIG. 1 in the process of seating the abutment in the implant.

The combination of the radially shaped annular outer surface 320 and the vertical stop surface 322 allows for a seal between abutment 104 and the implant 102. The vertical stop surface 322 prevents vertical location variability of the abutment 104 relative to the implant 102. The insertion of the abutment 104 in the implant 102 may be shown with reference to FIGS. 4A-4B and 5A-5C. FIGS. 4A-4B are perspective side cutaway views of the initial contact and final contact between abutment 104 and implant 102 in FIG. 1 while FIG. 5A-C are side cutaway views of the contacts between the abutment 104 and implant 102 in the process of locating the abutment 104 on the implant 102. For convenience of illustration, the groove 324 has been omitted from FIGS. 4A-4B and FIG. 5C. As shown in FIGS. 4A and 5A, the radially shaped outer surface 320 is inserted into the interface 208 of the implant 102 when the stem 304 is inserted in the cavity 214. The radially shaped outer surface 320 initially contacts the radially curved inner surface 230 of the interface 208. The abutment 104 is inserted into the implant 102 until the vertical stop surface 322 contacts the flat vertical stop surface 232 bordering the cavity 214 as shown in FIGS. 4B and 5B.

The radial interface 322 and the vertical stop surface 232 eliminate location variability from abutment 104 being seated in the implant 102. As may be seen in FIGS. 4 and 5, the vertical stop surface 232 of the implant 102 is connected to the radially curved inner surface 230. All the components in the restorative process requiring vertical location control use the vertical stop surface 232 for vertical location, so there is no error accumulated throughout the restorative process using the implant 102 and the abutment 104. During the restorative process involving the fabrication of the abutment 104, there is no contact with the radially curved sidewalls of the surface 320 for certain components because no seal is required. This is achieved in intermediate steps of the restorative process for these components by removing the radial interface on intermediate components such as the impression coping and the implant analog, thus ensuring that the abutment 104 contacts the vertical stop in the final assembly and prevent distortions from sidewall contact when using the intermediate components. Thus, the radially curved inner surface 230 of the implant 102 interfaces with the radially shaped outer surface 320 of the abutment 104, but the vertical position of the finish location is controlled by the radial interface 322 in contact with the vertical stop surface 232. This interface results in a first radial seal on the radially shaped outer surface 320 of the abutment 104 in contact with the radially curved inner surface 230 of the implant 102 as shown in FIG. 5C. A second horizontal seal on the bottom of the transitional section 310 is formed via the contact of the radial interface 322 of the abutment 104 with the vertical stop surface 232 of the implant 102.

Figure 4C:
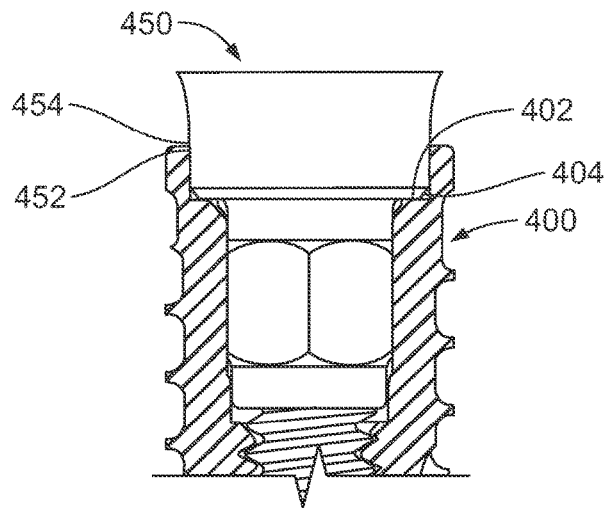
FIG. 4C-4E are side cutaway views of seating an alternate abutment in an alternate implant with a stop member for vertical location.
Figure 4D:
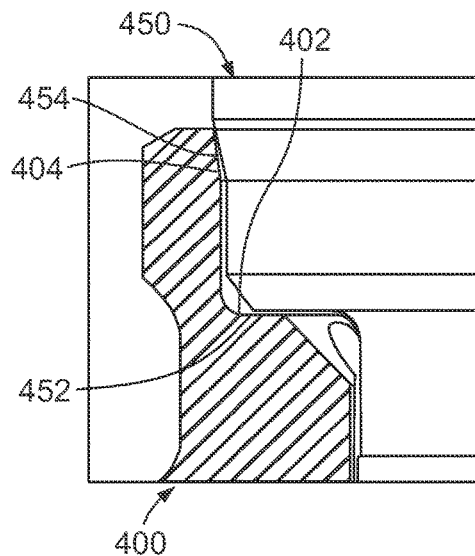
Figure 4E:
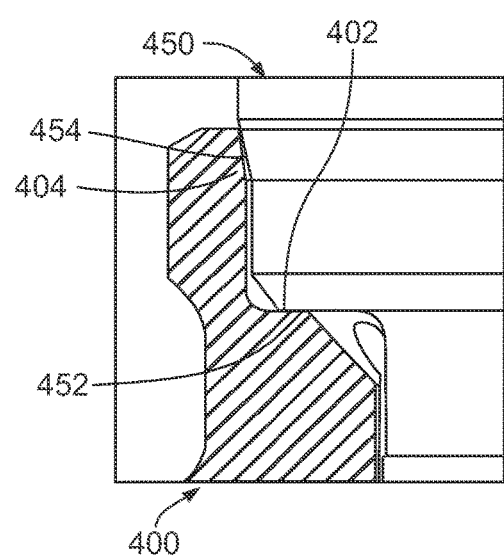

The radial interface 322 and the vertical stop surface 232 shown in FIG. 4A-4B and FIG. 5A-5C may be used with non-curved interfaces. FIG. 4C shows an implant 400 with a standard conical interface having a vertical stop surface 402 contacting an abutment 450. FIG. 4D is a close up view of the interface between the implant 400 and the abutment 450 prior to connection of the components while FIG. 4E is a close up view of the interface between the implant 400 and the abutment 450 when a seal has been established. The abutment 450 has a radial interface 452 that provides contact with the vertical stop surface 402. The vertical stop surface 402 eliminates location variability from the abutment 450 being seated in the implant 400. In this example, the abutment 450 has a standard conical interface surface 454 while the implant has a conical inner surface 404. As may be seen in FIGS. 4C and 4E, the vertical stop surface 402 of the implant 400 is connected to the conical inner surface 404. All the components in the restorative process requiring vertical location control use the vertical stop surface 402 for vertical location, so there is no error accumulated throughout the restorative process using the implant 400 and the abutment 450. During the restorative process involving the fabrication of the abutment 450, there is no contact with the conical surface 454 for certain components because no seal is required. This is achieved in intermediate steps of the restorative process for these components by removing the radial interface on intermediate components such as the impression coping and the implant analog, thus ensuring that the abutment 450 contacts the vertical stop surface 402 of the implant 400 in the final assembly and prevent distortions from sidewall contact when using the intermediate components. Thus, the conical inner surface 402 of the implant 400 interfaces with the conical surface 454 of the abutment 450, but the vertical position of the finish location is controlled by the vertical stop 402. A seal on the bottom of the transitional section of the abutment 450 is formed via the contact of the radial interface 452 of the abutment 450 with the vertical stop surface 402 of the implant 400. In this example, the angle of the conical inner surface 402 of the implant 400 is approximately 16 degrees while the angle of conical surface 454 of the abutment 450 is approximately 20 degrees. The lateral forces are concentrated at the top edge of the implant 400 on the conical inner surface 404 in order to aid in seating the abutment 450 in the implant 400. The contact between the conical inner surface 404 and the conical interface surface 454 also create another seal in addition to the seal between the radial interface 452 against the vertical stop surface 402.

A further benefit of better compliance is realized via the groove 324 on the abutment 104 shown in detail in FIGS. 3A-3D. The groove 324 allows a more compliant interface of the abutment 104 with the implant 102. Due to the groove 324, the interface formed by the radially curved surface 320 of the transitional section 310 has built in flexibility to compress into the groove 324 to allow the radially curved surface 320 to better conform to the radially curved inner surface 230 of the implant 102 and in turn increase the seal contact area between the abutment 104 and the implant 102. This flexibility is achieved by removing material from the cross-section of transitional section 310 of the abutment 104 to form the groove 324. Further, because the abutment 104 is compliant with the implant 102, the design may be manufactured more robustly, as the system will work under a wider range of tolerance configurations.

Figure 6A:
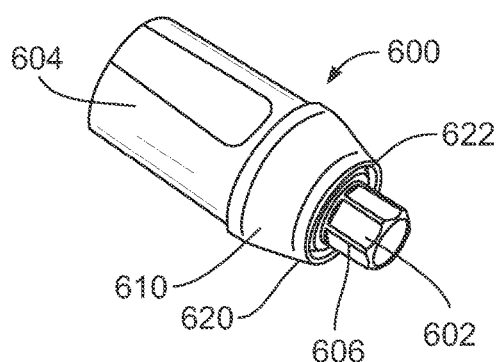
FIG. 6A is a perspective view of an alternate design for the abutment with a groove in the interface to facilitate fit into an implant.
Figure 6B:
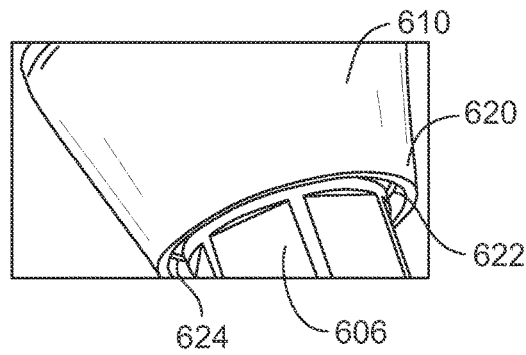
FIG. 6B is a side view of the abutment shown in FIG. 6A.
Figure 6C:
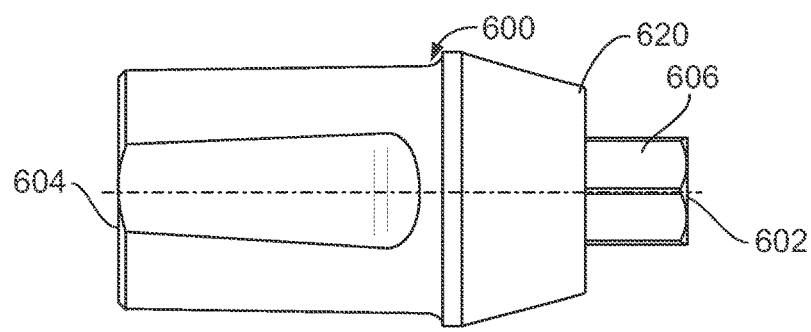
FIG. 6C is a cross-section side view of the abutment shown in FIG. 6A.
Figure 6D:
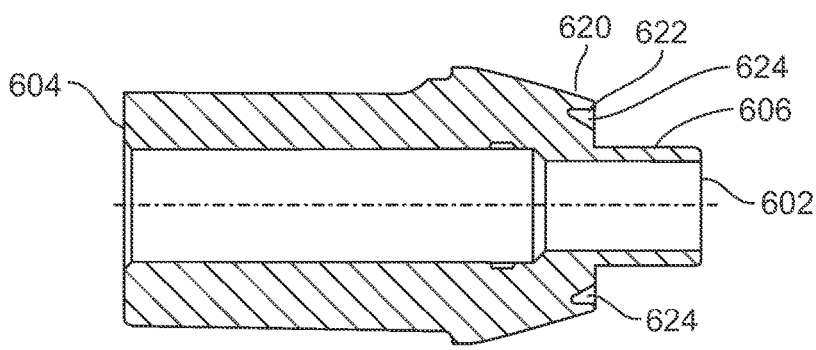
FIG. 6D is a close up perspective view of the groove on the alternate design for the abutment shown in FIG. 6A

The use of a groove such as the groove 324 shown in FIG. 3A-D in the interface of the abutment 104 may be used with conventional interfaces for vertical implant connection of abutments to any implant similar to the implant 102 in FIG. 1. For example, FIGS. 6A-6D are views of an abutment 600 having a conventional conical tapered interface but using the groove feature. FIG. 6A is a perspective view for the abutment 600 with a groove into the interface to the implant, FIG. 6B is a side view of the abutment 600 shown in FIG. 6A, FIG. 6C is a cross-section side view of the abutment 600 shown in FIG. 6A, and FIG. 6D is a close up perspective view of the groove on the alternate design for the abutment 600 shown in FIG. 6A.

The abutment 600 comprises a post 602 and a stem 604 extending in a relative downward direction from the post 602. The stem 604 includes a locking portion 606 adapted to be positioned in the first anti-rotation cavity 214 of the implant 102 when the abutment 104 is positioned in the implant 102. The locking portion 606 has a multi-sided exterior surface 608 that is adapted to rotationally-lockingly engage an interior multi-sided socketed surface such as the surface 220 of the first anti-rotation cavity 214 in FIG. 2C, wherein the abutment 600 is prevented from rotating relative to the implant.

The abutment 600 includes a transitional section 610 between the post 602 and the stem 604. The transitional section 610 mates with an exterior surface of the implant. The transitional section 610 includes an outer surface that generally slopes from a greater diameter closest to the post 602 to a smaller diameter close to the stem 604. A conically shaped outer surface 620 terminates into a circular vertical stop surface 622. The circular vertical stop surface 622 includes a circular groove 624. The circular groove 624 permits built in flexibility to allow the abutment 600 to better conform to the corresponding shaped inner surface of the implant and in turn increase the seal contact area between the abutment 600 and the implant.

Figure 7A:
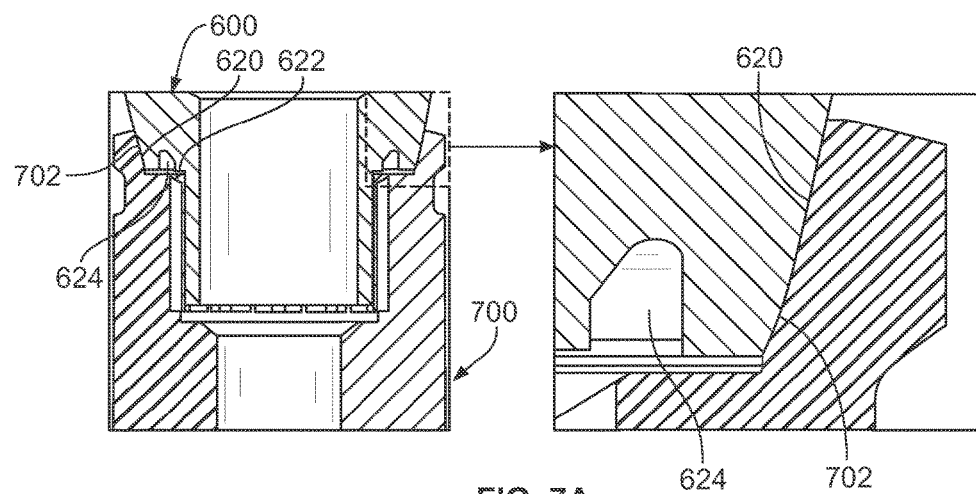
FIG. 7A is a side view of the alternate abutment design in FIG. 6A in contact with an implant.
Figure 7B:
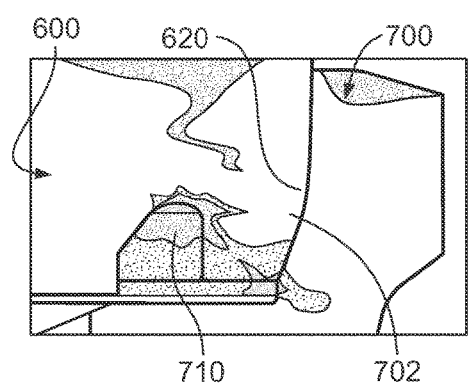
FIG. 7B is a stress diagram of the abutment in FIG. 6A in contact with the implant.

FIG. 7A is a side view of the abutment 600 in FIG. 6A in contact with an implant 700 and FIG. 7B is a stress diagram of the abutment 600 in contact with the implant 700. In this example, the implant 700 is similar to the implant 102, except that the implant 700 has a conventional conical interface surface 702. As may be seen in FIGS. 7A and 7B, a further benefit of better compliance is realized via the groove 624 on the abutment 600 which has a conventional conical interface surface 610. The inset portion of FIG. 7A is an extreme close up of the groove 624 cut into the transitional section 610. The groove 624 allows a more compliant interface of the abutment 600 with the implant 700. Due to the groove 624, the interface formed by the conically shaped outer surface 620 of the transitional section 610 has built in flexibility to compress into the groove 624 to allow the conically shaped outer surface 620 to better conform to the conically sloped interface inner surface 702 of the implant 700 and in turn increase the seal contact area between the abutment 600 and the implant 700. This flexibility is achieved by removing material from the cross-section of transitional section 610 of the abutment 600 to form the groove 624. Further, because the abutment is compliant with the implant 700, the design may be manufactured more robustly, as the system will work under a wider range of tolerance configurations. FIG. 7B shows compressive areas of stress 710 which are compressed from the conical sidewall 702 of the implant 700 pushing into the conically shaped outer surface 620 of the abutment 600.

Figure 8A:
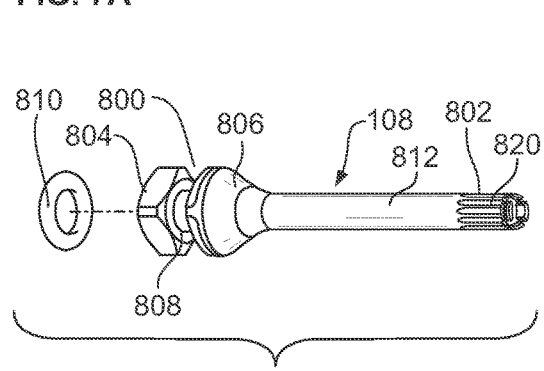
FIG. 8A is a perspective view of the implant driver tool shown in FIG. 1.
Figure 8B:
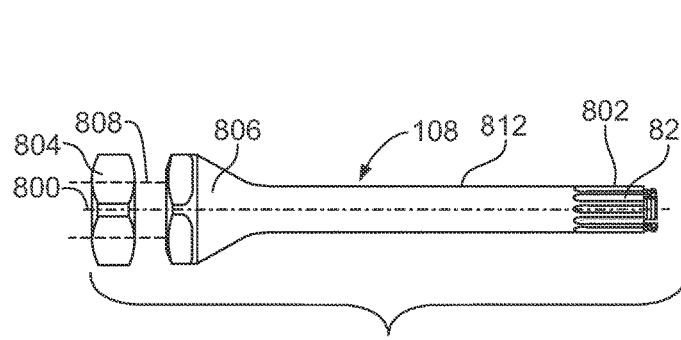
FIG. 8B is a side view of the implant driver tool shown in FIG. 8A.

FIG. 8A is a perspective view of the implant driver tool 108 shown in FIG. 1 and FIG. 8B is a side view of the implant driver tool 108. The implant driver tool 108 is adapted to mate with the first anti-rotation cavity 214 of the implant 102. When the implant driver tool 108 is mated with the implant 102, the driver tool 108 may be rotated to drive the threaded exterior surface 206 of the implant 102 into the bone. The implant driver tool 108 includes a first end 800 and a working end 802 that is adapted to fit within the bore 210 of the implant 102 in FIG. 2C. The first end 800 is a grip section that includes a wrench interface 804 that is spaced from a conical transition section 806 to form an annular groove 808. A resilient ring, such as an O-ring 810, is seated in the annular groove 808 to help retain the implant driver tool 108 in proper engagement with a torque wrench. The implant driver tool 108 has a shaft 812 having a proximal end coupled to the grip section of the first end 800 and a distal end that forms the working end 802. The distal end of the shaft 812 includes a hexagonal male geometry driver section 820 adapted to mate with the socketed interior surface 220 of the anti-rotation cavity 214 of the implant 102. The contact between the driver section 820 and the socketed interior surface 220 of the implant 102 allows the transition of torque force from the driver tool 108 to the implant 102.

Figure 8C:
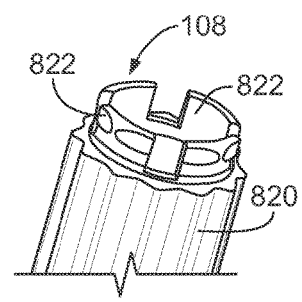
FIG. 8C is a close up view of the implant driver tool shown in FIG. 8A showing the members of the tip.

The wrench interface 804 of the implant driver tool 108 in this example has a four sided exterior surface to interface with a torque wrench that may be used to provide torque to turn the implant driver tool 108 and thereby the implant 102 to engage the threads on the exterior surface 206 with the bone to seat the implant 102. In order to maintain sterile conditions, the implant 102 is generally packed in a sterile package. The driver section 820 includes an end that is inserted in the bore 210 of the implant 102 to allow a user to hold the combined driver tool 108 and attached implant 102. The user may therefore use the implant driver tool 108 to move the implant 102 into the desired location in the bone without contacting the implant 102. FIG. 8C is a close up view of the end of the driver section 820 of the implant driver tool 108 shown in FIG. 8A showing a series of circumferential tips 822 extending from the exterior edge of the driving portion 820 of the working end 802. The diameter of the tips 822 in FIG. 8C are aligned with the counter bore 212 in the implant 102 to provide frictional contact thereby fixing the driver tool 108 to the implant 102.

The seal created by the interface 208 of the implant 102 with the abutment 104 creates the possibility of binding the abutment 104 to the implant 102 once assembled. In certain circumstances, such as replacement due to damage to the restoration, the abutment 104 requires removal from the implant 102. In some cases, the abutment 104 adheres to the implant 102 due to the sealing surfaces of the interface and cannot be removed manually. The abutment removal tool components 110 and 112 may then be used to insure that the abutment 104 may be removed without damaging or displacing the implant 102 if the abutment 104 remains adhered to the implant 102. As will be explained below, the abutment removal tool screw 112 is used in conjunction with the abutment removal insert tool 110 to engage the groove 328 within the through bore 326 of the abutment 104 as shown in FIG. 2C. The abutment removal tool screw 112 forces the abutment removal insert tool 110 into the groove 328 in the bore 326 of the abutment 104. The abutment removal tool insert 110 is prevented from rotating by securing the insert 110 by a wrench that causes the screw 112 to push against the bottom of the inside of the implant 102 when the abutment removal tool screw 112 is turned. The resulting downward force applied by the screw 112 against the implant 102 frees the abutment 104 from the implant 102.

The abutment removal tool screw 112 is shown in FIGS. 9A-9C where FIG. 9A is a perspective view of the abutment removal tool screw 112, FIG. 9B is a side view of the abutment removal tool screw 112, and FIG. 9C is a front view of the abutment removal tool screw 112. The abutment removal tool screw 112 includes a proximal end 902 and a distal end 904. The proximal end 902 includes a grip section 906 that includes a ridged outer surface that allows a grip for turning the abutment removal tool screw 112. The grip section 906 may also be mated with a torque imparting tool such as a wrench to turn the abutment removal tool screw 112. The grip section 906 is connected to a thread section 908 that includes exterior threads 910 that may be engaged with a threaded interior surface of the abutment removal insert tool 110 shown in FIGS. 10A-10E. The thread section 908 is connected to a shaft 912 that extends to the distal end 904.

Figure 10C:
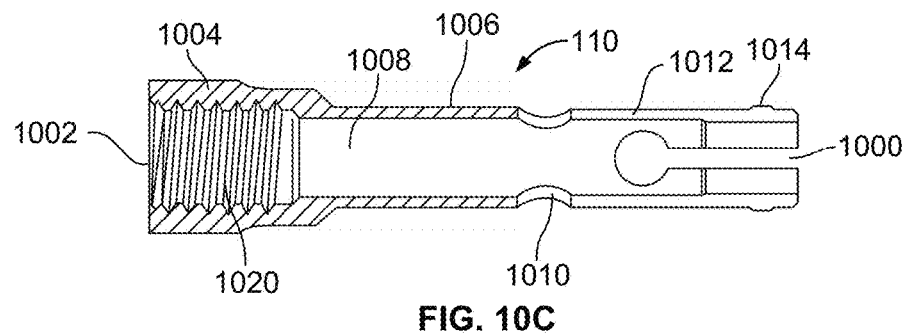
FIG. 10C is a cross-section side view of the abutment removal tool insert shown in FIG. 10A.
Figure 10D:
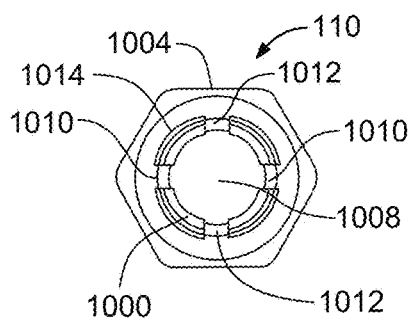
FIG. 10D is a front view of the abutment removal tool insert shown in FIG. 10A.
Figure 10E:
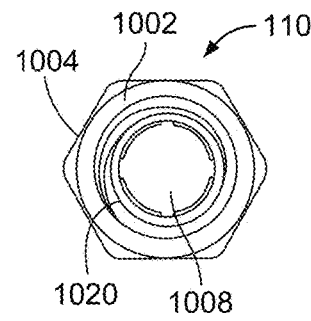
FIG. 10E is a back view of the abutment removal tool insert shown in FIG. 1.

FIGS. 10A-10E show the abutment removal insert tool 110 where FIG. 10A is a perspective view of the abutment removal insert tool 110, FIG. 10B is a side view of the abutment removal insert tool 110, FIG. 10C is a cross-section side view of the abutment removal insert tool 110 along the line 10C-10C' in FIG. 10B, FIG. 10D is a front view of the abutment removal insert tool 110, and FIG. 10E is a back view of the abutment removal insert tool 110. The abutment removal insert tool 110 includes a distal end 1000 and a proximal end 1002. A multi-sided interface 1004 is formed on the distal end 1000 to provide an interface for a wrench. A cylinder 1006 extends from the distal end 1000 to the proximal end 1002. The cylinder 1006 forms an interior bore 1008. Two long notches 1010 are cut from the proximal end 1002 and two short notches 1012 are cut from the proximal end 1002 over part of the length of the cylinder 1006. An annular protrusion 1014 extends out from the cylinder 1006 at the members formed by the notches 1010 and 1012. The end of the interior bore 1008 on the proximal end 1002 includes an interior threaded surface 1020.

Figure 11A:
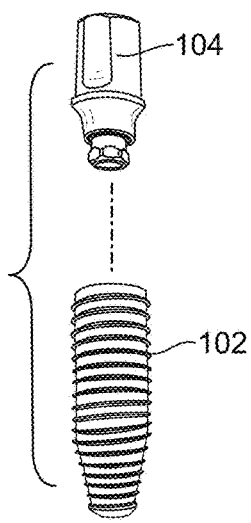
FIG. 11A-E are steps of the process of using the abutment removal tool implant and implant driver in FIG. 1 in separating the abutment from the insert.
Figure 11B:
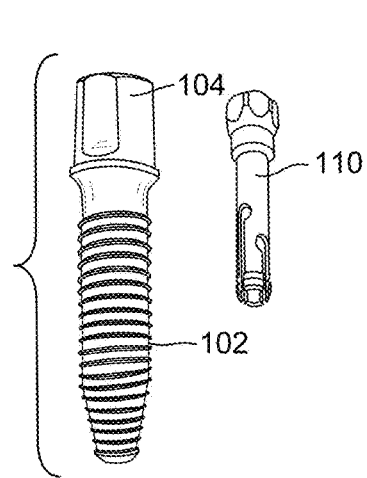

The process of removing the abutment 104 from the implant 102 using the abutment removal tool screw 112 and the abutment removal insert tool 110 is shown in FIGS. 11A-11E. FIG. 11A shows the abutment 104 and the implant 102 prior to connecting the abutment 104 to the implant 102 via the screw 106. FIG. 11B shows the abutment 104 has been assembled to the implant 102 with an abutment screw 106. If it is desired to remove the abutment 104, the abutment screw 106 is removed with a driver tool such as a screwdriver. After the abutment screw 106 is removed, the abutment 104 is stuck to the implant 102 due to excessive side contact and/or interference from the interface described above with reference to FIGS. 4 and 5. As explained above, the abutment removal insert tool 110 in conjunction with the abutment removal tool screw 112 are used to remove the abutment 104 from the implant 102.

Figure 11C:
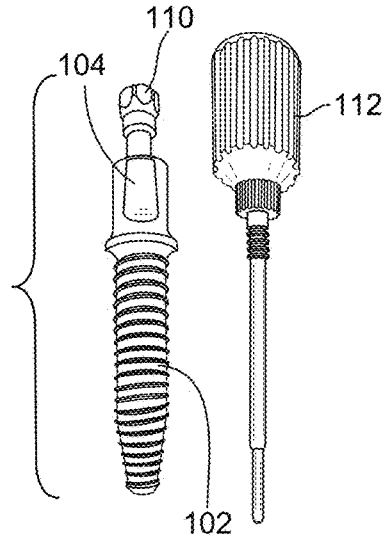

FIG. 11C shows the placement of the abutment removal insert tool 110 in the abutment 104. The protrusions 1014 at the distal end 1000 of the abutment removal insert tool 110 shown in FIG. 10A engage the groove 328 within the through-bore 326 of the abutment 104 shown in FIG. 3C. The abutment removal tool screw 112 is inserted in the interior bore 1008 of the abutment removal insert tool 110 and through the through-bore 326 of the abutment 104. The insertion of the abutment removal tool screw 112 in the interior bore 1008 of the abutment removal insert tool 110 forces the protrusions 1014 against the groove 328 thereby fixing the abutment removal insert tool 110 to the abutment 104.

Figure 11D:
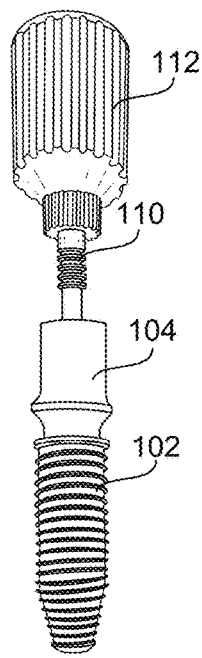

FIG. 11D shows the resulting placement of the abutment removal tool screw 112 into the abutment removal insert tool 110. The exterior threads 910 of the thread section 908 engage the interior threaded surface 1020 of the abutment removal insert tool 110. The distal end 1000 of the removal tool screw 112 is inserted through the interior bore 1008 of the abutment removal insert tool 110 to the implant 102.

Figure 11E:
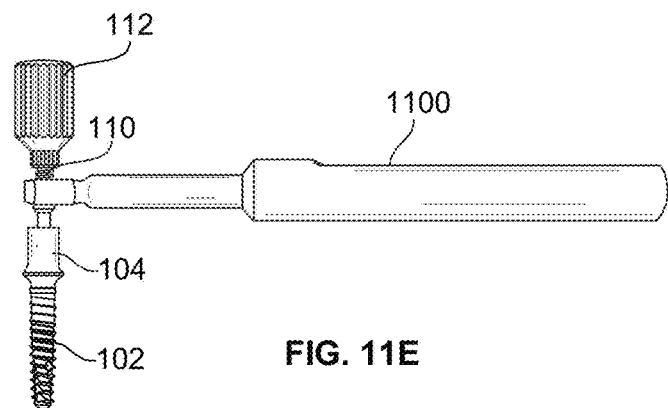

FIG. 11E shows the abutment removal insert tool 110 held with a wrench 1100 so that it and/or the implant 102 cannot rotate. A user then may grip the grip section 906 of the abutment removal tool screw 112 to turn the abutment removal tool screw 112. The distal end 1000 of the abutment removal tool screw 112 will contact the internal aspect of the implant 102. The resulting contact to the implant 102 will then apply a vertical force to the abutment 104 in relation to the implant 102 as further torque is applied to the abutment removal tool screw 112 translated through the thread section 908 to the interior threaded surface 1020 of the abutment removal insert tool 110. The abutment removal tool screw 112 is turned until the abutment 104 is freed from the implant 102.

Figure 12A:
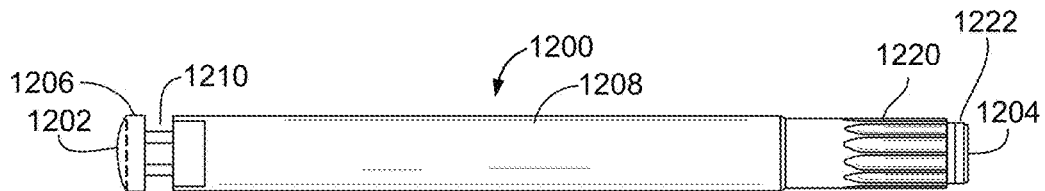
FIG. 12A is a perspective view of an alternate implant driver tool with a friction fit tapered nose.
Figure 12B:
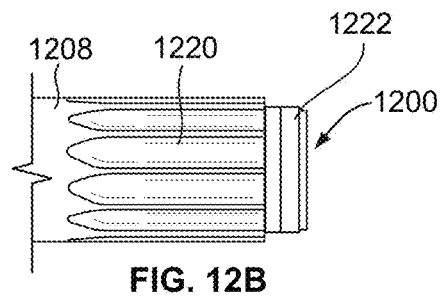
FIG. 12B is a close up view of the implant driver tool shown in FIG. 12A showing the fiction fit tapered nose of the tip.

Alternate designs may be made for each of the components shown in FIG. 1. For example, a different shaped driver tool may be used for the driver tool 108 such as the driver tool 1200 shown in FIGS. 12A and 12B, where FIG. 12A is a perspective view of the implant driver tool 1200 and FIG. 12B is a close up view of the implant driver tool 1200 shown in FIG. 12A. The implant driver tool 108 includes a first end 1202 and a working end 1204 that is adapted to fit within the bore 210 of the implant 102. The first end 1202 includes a wrench interface 1206 that is spaced from a shaft 1208 to form an annular groove 1210. A resilient ring, such as an O-ring (not shown) is seated in the annular groove 1210 to help retain the implant driver tool 1200 in proper engagement with a torque wrench. The working end 1204 of the implant driver tool 1200 has a hexagonal male geometry driving portion 1220 adapted to mate with the socketed interior surface 220 of the anti-rotation cavity 214 of the implant 102.

FIG. 12B is a close up view of the implant driver tool 1200 shown in FIG. 12A showing a friction fit tapered nose 1222 that replaces the tips 822 shown in FIG. 8C. The tapered nose 1222 fits within the counter bore 212 of the implant 102 and serves to hold the implant driver tool 1200 to the implant 102 to allow a user to manipulate the implant 102 while maintaining sterility of the implant 102. The advantage of the shape of the tapered nose 1222 is ease of manufacture of the implant driver tool 108.

Figures 12C, 12D:
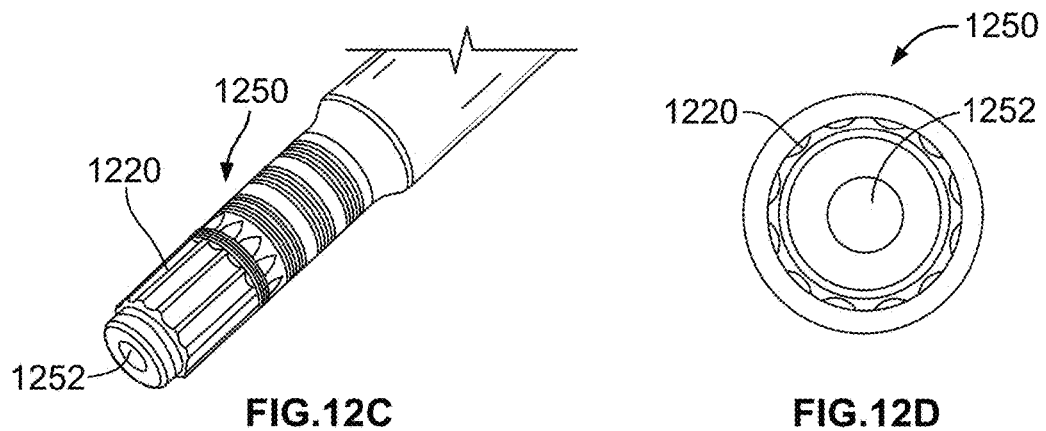
FIG. 12C is a close up view of the implant driver tool shown in FIG. 12A showing the fit taper nose with a bore.
FIG. 12D is a front view of the tip of the taper nose in FIG. 12C.

The implant driver tool 1200 shown in FIGS. 12A-12B may have alternative features of the tip to engage the implant to provide torque to the implant 102. An alternative tapered nose section 1250 is shown FIG. 12C which is a close up view of the tapered nose 1250 of the implant driver tool shown in FIG. 12A and FIG. 12D is a front view of the tip of the alternate tip configuration in FIG. 12C. Like elements are labeled with like element numbers in FIGS. 12C and 12D. The working end 1204 of the implant driver tool has a hexagonal male geometry driving portion 1220 adapted to mate with the socketed interior surface 220 of the anti-rotation cavity 214 of the implant 102. The alternative tapered nose 1250 has a circular bore 1252 as shown in FIG. 12D. The circular bore 1252 provides a reduction of the cross-sectional moment of inertia and reduces the stiffness of the tapered nose 1250 to decrease excessive contact between the tip and the implant 102.

Figure 13A:
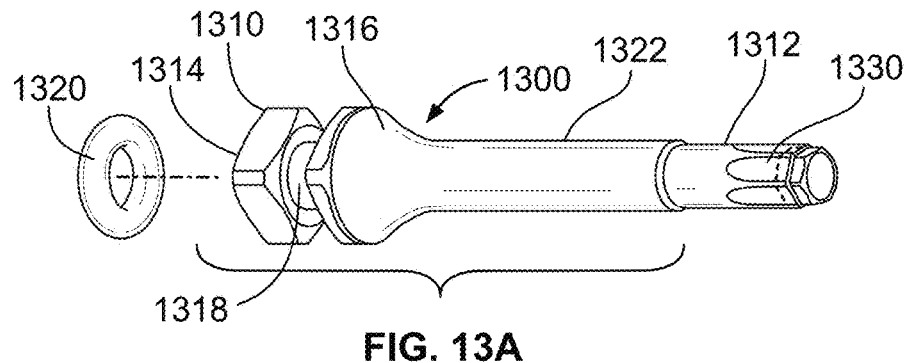
FIG. 13A is a perspective view of an alternate implant driver tool.
Figure 13B:
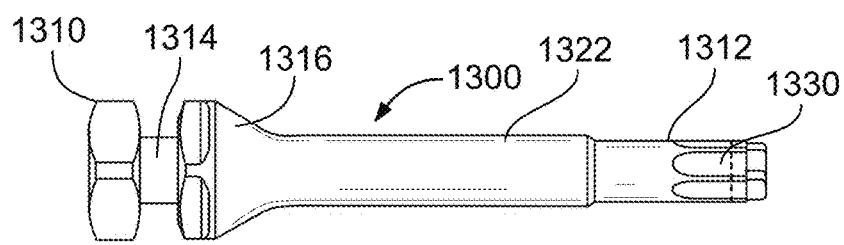
FIG. 13B is a side view of the implant driver tool shown in FIG. 13A.

FIG. 13A is a perspective view of an alternative implant driver tool 1300 that may be used instead of the implant driver tool 108 shown in FIG. 1. FIG. 13B is a side view of the implant driver tool 1300. The implant driver tool 1300 is adapted to mate with an anti-rotation cavity in an implant. When the implant driver tool 1300 is mated with the implant, the driver tool 1300 may be rotated to drive a threaded exterior surface of the implant into the bone. The implant driver tool 1300 includes a first end 1310 and a working end 1312 that is adapted to fit within the bore of an implant. The first end 1310 is a grip section that includes a wrench interface 1314 that is spaced from a conical transition section 1316 to form an annular groove 1318. A resilient ring, such as an O-ring 1320, is seated in the annular groove 1318 to help retain the implant driver tool 1300 in proper engagement with a torque wrench. The implant driver tool 1300 has a shaft 1322 having a proximal end coupled to the grip section of the first end 1310 and a distal end that forms the working end 1312. The distal end of the shaft 1322 includes a hexagonal male geometry driver section 1330 adapted to mate with a socketed interior surface of the anti-rotation cavity of the implant. The contact between the driver section 1330 and the socketed interior surface of the implant allows the transition of torque force from the driver tool 1300 to the implant.

The wrench interface 1314 of the implant driver tool 1300 in this example has a four sided exterior surface to interface with a torque wrench that may be used to provide torque to turn the implant driver tool 1300 and thereby the implant to engage the threads on the exterior surface with the bone to seat the implant. In order to maintain sterile conditions, the implant is generally packed in a sterile package. The driver section 1330 includes an end that is inserted in the bore of the implant to allow a user to hold the combined driver tool 1300 and attached implant. The user may therefore use the implant driver tool 1300 to move the implant into the desired location in the bone without contacting the implant.

Figures 13C, 13D:
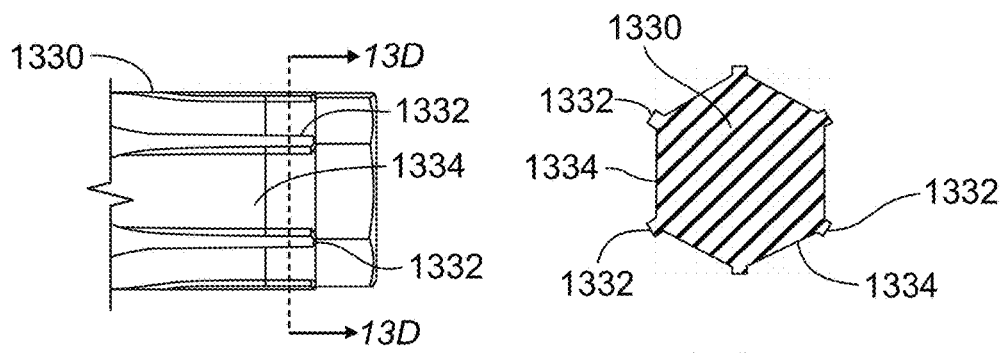
FIG. 13C is a close up view of the implant driver tool shown in FIG. 13A showing the members of the tip.
FIG. 13D is a front cross-section view of the tip of the implant driver tool shown in FIG. 13A from the perspective of the lines 13D-13D' in FIG. 13C.

FIG. 13C is a close up view of the end of the driver section 1330 of the implant driver tool 1300 shown in FIG. 13B. FIG. 13D is a close up front view of the driver section 1330 along the line 13D-13D' in FIG. 13C. The driver section 1330 has six tabs 1332 that extend out from the body of the driver section 1330. The six tabs 1332 are formed between sidewalls 1334 that contact similar surfaces in the socketed interior surface of the implant to connect the driver 1300 with the implant. The tabs 1332 are inserted in slots that are formed on the socket interior surface that provide additional contact between the driver 1300 and the implant. The driver section 1330 therefore has six points of contact in the form of the sidewalls 1334 as well as additional contacts from the six tabs 1332 contacting corresponding slots in the socket portion of the implant.

While particular implementations and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of the invention as defined in the appended claims.

What is claimed is:

1. A dental implant system, comprising:
   an implant including:
      a cylindrical body having an interior bore formed between a distal end and a proximal end;
      an abutment interface on the proximal end of the cylindrical body, the interface including a flat annular stop surface circumferentially bordering the interior bore; and
      an anti-rotational cavity formed in the interior bore between the distal end and the abutment interface;
   an abutment including:
      a stem;
      a post opposite of the stem;
      an interior bore formed through the stem and the post;
      an interface section between the post and the stem for interfacing with the dental implant, the interface section having an annular radial exterior surface between the post and the stem, the annular exterior surface having a curved convex transition surface terminating into a circular flat surface, the stem extending from the circular flat surface, the circular flat surface contacting the flat annular stop surface of the dental implant, and the curved convex transition surface interfacing with an interior mating surface of the dental implant including a corresponding concave surface; and
      an annular groove having at least one vertical surface cut into the circular flat surface to allow compliant fit of the interface section with the abutment interface of the implant when the abutment is inserted in the implant; and
   an implant driver tool including a tip to hold the dental implant, wherein the interior bore includes a counter-bore between the distal end and the anti-rotational cavity, the counter-bore having a narrower diameter than the anti-rotational cavity and sufficient to accept the tip of the implant driver tool to hold the dental implant to the implant driver tool via frictional contact with the counter-bore.

2. The dental implant system of claim 1, wherein the abutment interface further includes a radial annular interior surface bordering the interior bore.

3. The dental implant system of claim 1 further comprising an external screw thread on the exterior of the cylindrical body.

4. The dental implant system of claim 1, wherein the interior bore includes a second cavity including internal screw threads to accept a screw attaching the implant to an abutment.

5. The dental implant system of claim 1, wherein the cavity has a polygonal interior wall.

6. The dental implant system of claim 5, wherein the interior wall of the cavity forms a double sided hexagonal socket for attachment to an abutment.

7. A dental restoration system comprising:
   an implant for attachment to a jaw bone of a patient, the implant including:
      a cylindrical body having an interior bore formed between a distal end and a proximal end;
      an abutment interface on the proximal end of the cylindrical body, the abutment interface including an interior concave interface surface and a flat annular stop surface circumferentially bordering the interior bore;
      an anti-rotational cavity formed in the interior bore between the distal end and the abutment interface; and
   an abutment including:
      a stem;
      a post opposite the stem;
      an interior bore formed through the stem and the post; and
      an implant interface section between the post and the stem, the implant interface section interfacing with the abutment interface of the dental implant, the implant interface section including an annular convex exterior surface between the post and the stem, and a circular flat surface, wherein the circular flat surface has a groove having a vertical wall extending into the implant interface section to provide compliant fit when the annular convex exterior surface contacts the interior concave interface surface of the abutment interface of the implant and the flat annular stop surface of the implant interface section contacts the flat circular stop surface of the abutment interface such that a first portion of the circular flat surface on an inner side of the circular groove and a second portion of the circular flat surface on an outer side of the circular groove are both contacting the flat annular stop of the implant when the abutment is inserted in the implant.

8. The dental restoration system of claim 7, wherein the abutment interface includes a radial annular interior surface circumferentially bordering the interior bore.

* * * * *

UNITED STATES PATENT AND TRADEMARK OFFICE
CERTIFICATE OF CORRECTION

PATENT NO. : 10,201,405 B2
APPLICATION NO. : 13/533406
DATED : February 12, 2019
INVENTOR(S) : Bellanca et al.

Page 1 of 10

It is certified that error appears in the above-identified patent and that said Letters Patent is hereby corrected as shown below:

On the Title Page

In Column 2, under "U.S. Patent Documents", Line 1, before "5,447,434", insert:
--711,324 10/1902 Lacy 433/173
2,276,470 3/1942 Dodelin 81/451
3,514,858 6/1970 Silverman 32/2
3,618,212 11/1971 Weissman 32/10 A
3,643,658 2/1972 Steinemenan 128/92 D
3,726,011 4/1973 Savignano 32/10 A
3,760,502 9/1973 Hirsch 32/8
3,777,346 12/1973 Steinemann 29/180
3,919,723 11/1975 Heimke et al. 3/1.9
3,971,135 7/1976 Leu 32/48
4,011,602 3/1977 Rybicki et al. 3/1.9
4,040,129 8/1977 Steinemann et al. 3/1.9
4,072,070 2/1978 Finn 81/71
4,158,256 6/1979 Wiland et al. 32/12
4,179,810 12/1979 Kirsch 433/75
4,180,910 1/1980 Straumann et al. 433/173
4,185,383 1/1980 Heimke et al. 433/173
4,219,015 8/1980 Steinemann 128/92 D
4,234,309 11/1980 Sellers 433/225
4,293,302 10/1981 Hassler et al. 433/173
4,324,549 4/1982 Madray 433/169
4,328,593 5/1982 Sutter et al. 3/1.91
4,332,036 6/1982 Sutter et al. 3/1.91
4,380,436 4/1983 Kipp 433/182
4,388,921 6/1983 Sutter et al. 128/92 B
4,416,629 11/1983 Mozsary et al. 433/174
4,424,037 1/1984 Ogino et al. 433/173

Signed and Sealed this
Tenth Day of August, 2021

Drew Hirshfeld
*Performing the Functions and Duties of the
Under Secretary of Commerce for Intellectual Property and
Director of the United States Patent and Trademark Office*

4,444,310 1/1984 Odell 206/366
4,447,209 5/1984 Sutter 433/173
4,484,570 11/1984 Sutter et al. 128/92 D
4,486,178 12/1984 Schulte 433/173
4,490,116 12/1984 Deutsch et al. 433/215
4,540,367 9/1985 Sulc 433/181
4,560,353 12/1985 Schulte et al. 433/173
4,571,185 2/1986 Rota 433/173
4,591,483 5/1986 Nawaz 420/463
4,600,388 7/1986 Linkow 433/176
4,626,214 12/1986 Artal 433/174
4,657,510 4/1987 Gittleman 433/173
4,671,410 6/1987 Hansson et al. 206/438
4,671,768 6/1987 Ton 433/174
4,681,542 7/1987 Baum 433/172
4,687,443 8/1987 Driskell 433/173
4,710,075 12/1987 Davison 408/202
4,715,817 12/1987 Zuest et al. 433/181
4,712,681 12/1987 Branemark et al. 206/438
4,714,076 12/1987 Comte et al. 128/92
4,722,688 2/1988 Lonca 433/173
4,722,733 2/1988 Howson 604/411
4,731,085 3/1988 Koch 623/16
4,744,754 5/1988 Ross 433/173
4,756,691 7/1988 Pilarek 433/177
4,758,161 7/1988 Niznick 433/173
4,759,768 7/1988 Hermann et al. 623/21
4,763,788 8/1988 Jorneus et al. 206/438
4,772,204 9/1988 Söderberg 433/174
4,793,808 12/1988 Kirsch 433/173
4,803,976 2/1989 Frigg et al. 128/92
4,824,372 4/1989 Jörnéus et al. 433/174
4,826,434 5/1989 Krueger 433/174
4,846,683 7/1989 Lazzara et al. 433/173
4,850,870 7/1989 Lazzara et al. 433/174
4,850,873 7/1989 Lazzara et al. 433/220
4,854,872 8/1989 Detsch 433/173
4,856,648 8/1989 Krueger 206/63.5
4,856,994 8/1989 Lazzara et al. 433/173
4,865,648 9/1989 Kito et al. 106/21
4,872,839 10/1989 Brajnovic 433/173
4,875,475 10/1989 Comte et al. 128/924
4,880,006 11/1989 Albrektsson et al. 128/630
4,881,897 11/1989 Franek et al. 433/169
4,906,191 3/1990 Söderberg 433/213
4,906,420 3/1990 Brajnovic et al. 264/17

4,917,703 4/1990 Albrektsson 623/66
4,936,313 6/1990 Burkhardt et al. 128/751
4,955,811 9/1990 Lazzara et al. 433/173
4,960,381 10/1990 Niznick 433/174
4,978,007 12/1990 Jacobs et al. 206/469
4,983,184 1/1991 Steinemann 623/66
4,988,298 1/1991 Lazzara et al. 433/173
4,995,810 2/1991 Söderberg 433/141
5,000,685 3/1991 Brajnovic 433/173
5,002,542 3/1991 Frigg 606/61
5,006,069 4/1991 Lazzara et al. 433/173
5,006,070 4/1991 Komatsu 433/176
5,015,186 5/1991 Detsch 433/173
5,019,083 5/1991 Klapper et al. 606/99
5,022,860 6/1991 Lazzara et al. 433/174
5,026,285 6/1991 Dürr et al. 433/173
5,030,094 7/1991 Nardi et al. 433/169
5,030,096 7/1991 Hurson et al. 433/173
5,035,619 7/1991 Daftary 433/173
5,040,983 8/1991 Binon 433/173
5,045,054 9/1991 Hood et al. 604/22
5,049,072 9/1991 Lueschen 433/173
5,049,073 9/1991 Lauks 433/173
5,049,074 9/1991 Otani et al. 433/173
5,052,930 10/1991 Lodde et al. 433/173
5,052,931 10/1991 Kirsch 433/173
5,061,181 10/1991 Niznick 433/174
5,061,285 10/1991 Koch 623/16
5,062,800 11/1991 Niznick 433/229
5,064,375 11/1991 Jorneus 433/229
5,069,622 12/1991 Rangert et al. 433/173
5,071,350 12/1991 Niznick 433/173
5,071,351 12/1991 Green, Jr. et al. 433/173
5,073,111 12/1991 Daftary 433/173
5,076,788 12/1991 Niznick 433/173
5,078,605 1/1992 Sutter et al. 433/165
5,080,685 1/1992 Bolesky et al. 623/23
RE33,796 1/1992 Niznick 433/173
5,100,323 3/1992 Friedman et al. 433/173
5,105,690 4/1992 Lazzara et al. 81/436
5,106,300 4/1992 Voitik 433/173
5,116,225 5/1992 Riera 433/173
5,120,221 6/1992 Orenstein et al. 433/159
5,120,222 6/1992 Sulc 433/181
5,122,059 6/1992 Dürr et al. 433/173
5,125,840 6/1992 Dürr et al. 433/173

CERTIFICATE OF CORRECTION (continued)
U.S. Pat. No. 10,201,405 B2

5,125,841 6/1992 Carlsson et al. 433/213
5,135,395 8/1992 Marlin 433/174
5,140,877 8/1992 Sloan 81/439
5,145,371 9/1992 Jörnéus 433/173
5,145,372 9/1992 Daftary et al. 433/173
5,154,612 10/1992 Carlsson et al. 433/173
5,158,458 10/1992 Perry 433/141
5,174,755 12/1992 Fukuda 433/173
5,158,458 10/1992 Perry 433/141
5,180,303 1/1993 Homburg et al. 433/173
5,181,928 1/1993 Bolesky et al. 623/23
5,188,800 2/1993 Green, Jr. et al. 422/23
5,190,543 3/1993 Schläpfer 606/61
5,195,891 3/1993 Sulc 433/173
5,195,892 3/1993 Gersberg 433/174
5,196,016 3/1993 Buser et al. 606/72
5,197,881 3/1993 Chalifoux 433/173
5,199,873 4/1993 Schulte et al. 433/174
5,209,659 5/1993 Friedman et al. 433/173
5,209,666 5/1993 Balfour et al. 433/173
5,211,561 5/1993 Graub 433/169
5,213,500 5/1993 Salazar et al. 433/169
5,213,502 5/1993 Daftary 433/172
5,215,460 6/1993 Perry 433/75
5,238,405 8/1993 Marlin 433/173
D339,419 9/1993 Hood et al. D24/146
5,246,368 9/1993 Sillard 433/167
5,246,370 9/1993 Coatoam 433/173
D340,981 11/1993 Hood et al. D24/146
D341,201 11/1993 Hood et al. D24/146
D341,202 11/1993 Hood et al. D24/146
D342,313 12/1993 Hood et al. D24/146
5,281,140 1/1994 Niznick 433/172
5,286,195 2/1994 Clostermann 433/172
5,292,252 3/1994 Nickerson et al. 433/173
5,295,831 3/1994 Patterson et al. 433/141
5,297,963 3/1994 Daftary 433/172
5,302,125 4/1994 Kownacki et al. 433/172
5,302,126 4/1994 Wimmer et al. 433/173
5,306,149 4/1994 Schmid et al. 433/173
5,312,253 5/1994 Chalifoux 433/173
5,312,254 5/1994 Rosenlicht 433/173
5,312,403 5/1994 Frigg 606/54
5,316,476 5/1994 Krauser 433/173
5,318,570 6/1994 Hood et al. 606/99
5,322,443 6/1994 Beaty 433/141

5,324,297 6/1994 Hood et al. 606/99
5,328,371 7/1994 Hund et al. 433/173
5,334,024 8/1994 Niznick 433/173
5,336,090 8/1994 Wilson, Jr. et al. 433/172
5,338,196 8/1994 Beaty et al. 433/172
5,344,457 9/1994 Pilliar et al. 623/16
5,362,234 11/1994 Salazar et al. 433/169
5,362,237 11/1994 Chalifoux 433/220
5,368,160 11/1994 Leuschen et al. 206/339
5,368,443 11/1994 Turkia et al. 416/184
5,368,480 11/1994 Balfour et al. 433/141
5,368,483 11/1994 Sutter et al. 433/173
5,376,004 12/1994 Mena 433/173
5,387,102 2/1995 Wagner et al. 433/173
5,399,090 3/1995 Padros-Fradera 433/173
5,403,136 4/1995 Mathys 411/310
5,417,570 5/1995 Zuest et al. 433/177
5,419,702 5/1995 Beaty et al. 433/214
5,431,567 7/1995 Daftary 433/172
5,433,607 7/1995 Schmid et al. 433/173
5,433,665 7/1995 Beaty et al. 464/38
5,437,550 8/1995 Beaty et al. 433/141
5,437,551 8/1995 Chalifoux 433/173--

In Column 2, under "U.S. Patent Documents", Line 2, before "5,527,182", insert:
--5,449,291 9/1995 Lueschen et al. 433/173
5,452,219 9/1995 Dehoff et al. 364/474.05
5,456,723 10/1995 Steinemann et al. 623/16
5,462,436 10/1995 Beaty 433/141
5,468,150 11/1995 Brammann 433/173
5,476,383 12/1995 Beaty et al. 433/214
5,489,210 2/1996 Hanosh 433/173
5,492,471 2/1996 Singer 433/172
5,502,087 3/1996 Tateosian et al. 523/115
5,520,689 5/1996 Schläpfer et al. 606/61--

On the page 2, in Column 1, under "U.S. Patent Documents", Line 1, before "5,695,335", insert:
--5,538,426 7/1996 Harding et al. 433/172
5,538,428 7/1996 Staubli 433/173
5,547,377 8/1996 Daftary 433/172
5,554,028 9/1996 Hare et al. 433/214
5,556,280 9/1996 Pelak 433/172
5,562,448 10/1996 Mushabac 433/215
5,562,733 10/1996 Weissbach et al. 623/16
5,564,921 10/1996 Marlin 433/172
5,564,924 10/1996 Kwan 433/173

5,567,155 10/1996 Hansen 433/172
5,569,035 10/1996 Balfour et al. 433/165
5,571,188 11/1996 Ellingsen et al. 623/16
5,582,299 10/1996 Lazzara et al. 206/63.5
5,588,838 12/1996 Hansson et al. 433/173
5,591,029 1/1997 Zuest 433/173
5,605,457 2/1997 Bailey et al. 433/174
5,607,304 3/1997 Bailey et al. 433/174
5,626,227 5/1997 Wagner et al. 206/369
5,628,630 5/1997 Misch et al. 433/174
5,630,717 5/1997 Zuest et al. 433/172
5,636,989 6/1997 Somborac et al. 433/173
5,651,675 7/1997 Singer 433/172
5,658,147 8/1997 Phimmasone 433/213
5,660,545 8/1997 Bailey et al. 433/173
5,662,476 9/1997 Inger et al. 433/213
5,667,384 9/1997 Sutter et al. 433/172
5,674,069 10/1997 Osorio 433/172
5,674,071 10/1997 Beaty et al. 433/172
5,674,072 10/1997 Moser et al. 433/173
5,674,073 10/1997 Ingber et al. 433/213
5,674,244 10/1997 Mathys 606/208
5,678,995 10/1997 Kirsch et al. 433/169
5,681,167 10/1997 Lazarof 433/174
5,685,715 11/1997 Beaty et al. 433/173
5,688,123 11/1997 Meiers et al. 433/173
5,692,904 12/1997 Beaty et al. 433/141--

On the page 2, in Column 1, under "U.S. Patent Documents", Line 2, before "5,823,776", insert:
--5,704,788 1/1998 Milne 433/173
5,725,377 3/1998 Lemler et al. 433/173
5,730,598 3/1998 Story et al. 433/201.1
5,733,122 3/1998 Gordon 433/172
5,733,123 3/1998 Blacklock et al. 433/173
5,734,113 3/1998 Vogt et al. 73/862.23
5,741,253 4/1998 Michelson 606/61
5,749,731 5/1998 Morgan et al. 433/173
5,752,830 5/1998 Suarez 433/173
5,752,831 5/1998 Padros-Fradera 433/173
5,755,574 5/1998 D'Alise 433/173
5,755,807 5/1998 Anstaett et al. 623/23
5,759,033 6/1998 Elia 433/173
5,759,034 6/1998 Daftary 433/173
5,759,036 6/1998 Hinds 433/214
5,762,500 6/1998 Lazarof 433/213
5,762,541 6/1998 Heath et al. 451/48

5,766,009 6/1998 Jeffcoat 433/173
5,779,480 7/1998 Groll et al. 433/173
5,782,637 7/1998 Cosenza 433/173
5,782,918 7/1998 Klardie et al. 623/16
5,785,525 7/1998 Weissman 433/174
5,810,589 9/1998 Michnick et al. 433/169
5,810,590 9/1998 Fried et al. 433/172
5,816,812 10/1998 Kownacki et al. 433/174
5,820,374 10/1998 Simmons et al. 433/173--

On the page 2, in Column 1, under "U.S. Patent Documents", Line 3, before "5,888,218", insert:
--5,823,777 10/1998 Misch et al. 433/174
5,827,062 10/1998 Driskell et al. 433/173
5,829,977 11/1998 Rogers et al. 433/172
5,829,981 11/1998 Ziegler 433/214
5,836,768 11/1998 Hüskens et al. 433/173
D401,695 11/1998 Daftary D24/155
5,842,865 12/1998 Bassett et al. 433/174
5,858,253 1/1999 Holm 210/702
5,865,622 2/1999 Aleksey 433/177
D405,179 2/1999 Kirsch et al. D24/154
5,871,358 2/1999 Ingber et al. 433/213
5,871,504 2/1999 Eaton et al. 606/232
5,882,200 3/1999 Sutter et al. 433/173--

On the page 2, in Column 1, under "U.S. Patent Documents", Line 4, before "D414,556", insert:
--5,897,320 4/1999 Gittleman 433/180
5,899,940 5/1999 Carchidi et al. 623/16
5,904,483 5/1999 Wade 433/173
D410,083 5/1999 Broberg et al. D24/156
5,906,488 5/1999 Kvarnström 433/116
5,915,968 6/1999 Kirsch et al. 433/173
5,927,979 7/1999 Misch et al. 433/173
5,931,674 8/1999 Hanosh et al. 433/173
5,938,443 8/1999 Lazzara et al. 433/173
5,938,444 8/1999 Hansson et al. 433/174
5,938,446 8/1999 Andersson et al. 433/223
5,944,526 8/1999 Liu 433/176
5,947,733 9/1999 Sutter et al. 433/173
5,947,734 9/1999 Hanel 433/173
5,947,736 9/1999 Behrend 433/214
5,951,287 9/1999 Hawkinson 433/173
5,951,288 9/1999 Sawa 433/173--

On the page 2, in Column 1, under "U.S. Patent Documents", Line 33, before "6,168,436", insert:
--6,083,004 7/2000 Misch et al. 433/173

CERTIFICATE OF CORRECTION (continued)
U.S. Pat. No. 10,201,405 B2

6,086,371 7/2000 Bassett et al. 433/173
6,093,023 7/2000 Sala Meseguer 433/173
6,099,311 8/2000 Wagner et al. 433/163
6,102,702 8/2000 Folsom, Jr. et al. 433/172
6,116,904 9/2000 Kirsch et al. 433/173
6,120,292 9/2000 Buser et al. 433/173
6,142,782 11/2000 Lazarof 433/174
6,146,387 11/2000 Trott et al. 606/104
6,149,432 11/2000 Shaw et al. 433/174
6,149,433 11/2000 Ziegler et al. 433/214
6,155,828 12/2000 Lazzara et al. 433/173
6,159,008 12/2000 Kumar 433/163
6,159,244 12/2000 Suddaby 623/17.11--

On the page 2, in Column 1, under "U.S. Patent Documents", Line 34, before "6,257,890", insert:
--6,193,516 2/2001 Story 433/173
6,196,842 3/2001 Jörnéus 433/174
6,203,323 3/2001 Beaty et al. 433/173
6,206,696 3/2001 Day 433/141
6,208,813 3/2001 Carlsson et al. 396/324
6,213,773 4/2001 Gittleman 433/172
6,214,007 4/2001 Anderson, David G
6,217,331 4/2001 Rogers et al. 433/173
6,217,332 4/2001 Kumar 433/173
6,220,860 4/2001 Hansson 433/173
6,227,858 5/2001 Lundgren 433/173
6,227,859 5/2001 Sutter 433/173
6,231,342 5/2001 Osorio et al. 433/173
6,247,933 6/2001 Wagner et al. 433/173
6,254,387 7/2001 Bergström et al. 433 49--

On the page 2, in Column 2, under "U.S. Patent Documents", Line 20, before "2004/0101808", insert:
--6,726,481 4/2004 Zickmann et al. 433/173
6,733,291 5/2004 Hurson 433/173
7,101,183 9/2006 Augthun et al. 433/173
7,214,063 5/2007 Cohen 433/174
7,309,231 12/2007 Engman 433/173
7,338,286 3/2008 Porter et al. 433/173
7,344,376 3/2008 Beaty et al. 433/173
7,484,959 2/2009 Porter et al. 433/173
7,665,990 2/2010 Mundwiler et al. 433/173
8,033,826 10/2011 Towse et al. 433/172
8,070,491 12/2011 Mundwiler et al. 433/163
8,113,835 2/2012 Yau et al. 433/173
2001/0004694A1 6/2001 Carchidi, Joseph Edward, et al.
2001/0037154 11/2001 Martin 623/20.12

CERTIFICATE OF CORRECTION (continued)
U.S. Pat. No. 10,201,405 B2

2002/0025505 2/2002 Beaty et al. 433/173
2002/0106610 8/2002 Hurson 433/173
2003/0224327 12/2003 Constantino 433/165
2004/0038179 2/2004 Kumar et al. 433/173--

On the page 2, in Column 2, under "U.S. Patent Documents", Line 21, before "2008/0261176", insert:
--2005/0008990A1 1/2005 Ganz, Scott D, et al.
2005/0084820A1 4/2005 Ashman. Arthur. et al.
2005/0113930A1 5/2005 Ganz, Scott D, et al.
2005/0191600A1 9/2005 Beaty, Keith D, et al.
2005/0214714A1 9/2005 Wohrle, PeterS
2007/0142789A1 6/2007 Fisher, Mark James. et al.
2008/0057477A1 3/2008 Rosen, Dan
2008/0102420A1 5/2008 Porter, Stephan S, et al.
2008/0153062A1 6/2008 Beaty, Keith D, et al.
2008/0182227 7/2008 Wolf et al. 433/174
2008/0243123A1 10/2008 Wallis, Antonio Jose Gordils, et al.--

On the page 2, in Column 2, under "U.S. Patent Documents", Line 22, before "2010/0119995", insert:
--2009/0111072 4/2009 Lombardo et al. 433/174--

On the page 2, in Column 2, under "U.S. Patent Documents", Line 23, before "2013/0004916", insert:
--2010/0248180 9/2010 Bondar 433/141
2010/0266985 10/2010 Yau et al. 433/173
2010/0330531 12/2010 Olsson et al.
2011/0008754A1 1/2011 Bassett, Jeffrey A, et al.
2011/0183290 7/2011 Galgut et al. 433/174
2011/0250564 10/2011 Hung 433/174
2012/0077151 3/2012 Nary Filho et al. 433/174--

On the page 2, in Column 2, under "Foreign Patent Document", Line 3, before "EP", insert:
--DE 102009015358 9/2010--

On the page 2, in Column 2, under "Foreign Patent Document", Line 17, before "WO", insert:
--FR 2695823 3/1994
JP 11501856A 2/1999
JP 2003190188A 7/2003
JP 2004141479A 5/2004
JP 2009504248A 2/2009
JP 2010136943A 6/2010
JP 2014520599A 8/2014--

On the page 2, in Column 2, under "Foreign Patent Document", Line 23, before "WO", insert:
--WO 9724996A2 7/1997--

CERTIFICATE OF CORRECTION (continued)
U.S. Pat. No. 10,201,405 B2

On the page 2, in Column 2, under "Foreign Patent Document", Line 29, before "WO", insert:
--WO 2007021519A2 2/2007--

On the page 2, in Column 2, under "Other Publications", Line 7, after "(13 pages)", insert:
--"U.S. Appl. No. 13/533,463, Notice of Allowance dated Nov. 8, 2017", 8 pgs
"U.S. Appl. No. 13/533,463, Response filed Oct. 25, 2017 to Final Office Action dated Aug. 28, 2017", 8 pgs.
"U.S. Appl. No. 13/533,463, Advisory Action dated Nov. 30, 2016", 3 pgs
"U.S. Appl. No. 13/533,463, Final Office Action dated Aug. 23, 2016", 9 pgs
"U.S. Appl. No. 13/533,463, Final Office Action dated Aug. 28, 2017"', 14 pgs
"U.S. Appl. No. 13/533,463, Non Final Office Action dated Jan. 6, 2016", 9 pgs
"U.S. Appl. No. 13/533,463, Non Final Office Action dated Feb. 28, 2017", 8 pgs
"U.S. Appl. No. 13/533,463, Response filed May 6, 2016 to Non Final Office Action dated Jan. 6, 2016", 14 pgs.
"U.S. Appl. No. 13/533,463, Response filed May 15, 2017 to Non Final Office Action dated Feb. 28, 2017", 13 pgs.
"U.S. Appl. No. 13/533,463, Response filed Oct. 24, 2016 to Final Office Action dated Aug. 23, 2016", 15 pgs.
"U.S. Appl. No. 13/533,463, Response filed Nov. 25, 2014 to Restriction Requirement dated Nov. 3, 2014", 6 pgs
"U.S. Appl. No. 13/533,463, Response filed Dec. 9, 2016 to Advisory Action dated Nov. 30, 2016", 16 pgs
"U.S. Appl. No. 13/533,463, Restriction Requirement dated Nov. 3, 2014", 6 pgs
"International Application Serial No. PCT/US2012/044308, International Preliminary Report on Patentability dated Jan. 16, 2014", 12 pgs
"Australian Application Serial No. 2012275524, First Examiner Report dated Apr. 21, 2016", 4 pgs
"Australian Application Serial No. 2012275524, Response filed Jan. 10, 2017 to First Examiner Report dated Apr. 21, 2016", 46 pgs
"European Application Serial No. 12804137.3, Extended European Search Report dated Mar. 10, 2015", 13 pgs
"European Application Serial No. 12804137.3, Office Action dated Feb. 7, 2014", 3 pgs
"European Application Serial No. 12804137.3, Office Action dated Mar. 27, 2015", 1 pgs
"European Application Serial No. 12804137.3, Response filed Aug. 7, 2014 to Office Action dated Feb. 7, 2014", 10 pgs
"European Application Serial No. 12804137.3, Response filed Sep. 30, 2015 to Office Action dated Mar. 27, 2015", 13 pgs
"Japanese Application Serial No. 2014-518938, Office Action dated Feb. 13, 2017", (W/English Translation), 14 pgs
"Japanese Application Serial No. 2014-518938, Office Action dated Mar. 22, 2016", (W/English Translation), 10 pgs
"Japanese Application Serial No. 2014-518938, Response filed Sep. 14, 2016 to Office Action dated Mar. 22, 2016", W/English Translation Of Claims, 21 pgs
Supplementary European Search Report, Application No. 12804137.3, dated Nov. 6, 2014, 6 pages.--